US012661279B2

(12) United States Patent
Li et al.

(10) Patent No.: US 12,661,279 B2
(45) Date of Patent: Jun. 23, 2026

(54) FLUID MANAGEMENT LAYER FOR AN ABSORBENT ARTICLE, AND AN ABSORBENT ARTICLE CONTAINING THE SAME

(71) Applicant: The Procter & Gamble Company, Cincinnati, OH (US)

(72) Inventors: Wanning Li, Beijing (CN); Xiaoxin Liu, Beijing (CN); Kun Sun, Beijing (CN); Gerard Alain Viens, Wyoming, OH (US); Fancheng Wang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 357 days.

(21) Appl. No.: 18/137,478

(22) Filed: Apr. 21, 2023

(65) Prior Publication Data

US 2023/0346613 A1 Nov. 2, 2023

(30) Foreign Application Priority Data

Apr. 27, 2022 (WO) ................ PCT/CN2022/089502

(51) Int. Cl.
A61F 13/537 (2006.01)
A61F 13/15 (2006.01)

(52) U.S. Cl.
CPC .... A61F 13/53747 (2013.01); A61F 13/5376 (2013.01); A61F 2013/15406 (2013.01);
(Continued)

(58) Field of Classification Search
CPC .......... A61F 13/53708; A61F 13/53713; A61F 13/53747; A61F 13/5376;
(Continued)

(56) References Cited

U.S. PATENT DOCUMENTS

| | | | | |
|---|---|---|---|---|
| 5,458,835 A | * | 10/1995 | Wilkes | A61L 15/28 264/188 |
| 5,599,335 A | * | 2/1997 | Goldman | A61L 15/42 604/378 |

(Continued)

FOREIGN PATENT DOCUMENTS

| | | |
|---|---|---|
| CN | 106521811 B | 8/2019 |
| JP | 2015067936 A | 4/2015 |
| WO | 2007035038 A1 | 3/2007 |

OTHER PUBLICATIONS

Search Report and Written Opinion for PCT/CN2022/089502 dated Oct. 17, 2022,13 pages.

*Primary Examiner* — Michele Kidwell
(74) *Attorney, Agent, or Firm* — Anna E. Haller; Angela K. Haughey

(57) ABSTRACT

The present invention relates to a nonwoven sheet from about 10% to about 60% of non-swelling wicking fibers, from about 15% to about 70% of resilient fibers, and from about 25% to about 70% of stiffening fibers by weight of fluid the nonwoven as determined by the Material Composition Analysis, and wherein the non-swelling wicking fibers have a relative shape factor in radius in the range of about 25% to about 100% as determined the Relative Shape Factor in Radius test, and have a linear density of 0.8 dtex to 3.3 dtex as determined the Fiber Decitex test; and an absorbent article comprising a liquid permeable topsheet, a liquid impermeable backsheet, an absorbent core disposed between the topsheet and the backsheet, and a fluid management layer disposed between the topsheet and the absorbent core, the fluid management layer comprising the nonwoven sheet disclose herein.

20 Claims, 7 Drawing Sheets

(52) U.S. Cl.
CPC ............... *A61F 2013/15447* (2013.01); *A61F 2013/1552* (2013.01); *A61F 2013/15983* (2013.01); *A61F 2013/53795* (2013.01)

(58) Field of Classification Search
CPC ............ A61F 2013/15406; A61F 2013/15447; A61F 2013/1552; A61F 2013/15983; A61F 2013/53795; D04H 1/435; D04H 1/43912; D04H 1/43914; D04H 1/49; D04H 1/498; D04H 1/5412
See application file for complete search history.

(56) References Cited

U.S. PATENT DOCUMENTS

| | | | |
|---|---|---|---|
| 2003/0208175 A1 * | 11/2003 | Gross | A61F 13/534 604/378 |
| 2012/0238982 A1 | 9/2012 | Weisman et al. | |
| 2014/0343523 A1 * | 11/2014 | Viens | D04H 1/498 162/146 |
| 2020/0315871 A1 * | 10/2020 | Viens | A61F 13/15203 |
| 2020/0315872 A1 * | 10/2020 | Viens | A61F 13/535 |

* cited by examiner

9003

9010    9010

9012

9011

9012

L 9010    9010

W          2013

9001

9002          9007          9002

65°    9009

65°    9003
9005

FLUID MANAGEMENT LAYER FOR AN ABSORBENT ARTICLE, AND AN ABSORBENT ARTICLE CONTAINING THE SAME

CROSS-REFERENCE TO RELATED APPLICATIONS

This application claims priority under 35 U.S.C. § 119 to Chinese PCT Patent Application Serial No. PCT/CN2022/089502, filed on Apr. 27, 2022, the entire disclosures of which are hereby incorporated by reference.

TECHNICAL FIELD

The present disclosure generally relates to fluid management layers for disposable absorbent articles, in particular, fluid management layers that are nonwovens having improved performance characteristics.

BACKGROUND

Disposable absorbent articles such as feminine hygiene products, taped diapers, pant-type diapers and incontinence products are designed to absorb fluids from the wearer's body. Users of such disposable absorbent articles have several concerns. Leakage from products like catamenial pads, diapers, sanitary napkins, and incontinence pads is a significant concern. Comfort and the feel of the product against the wearer's body is also a concern. To provide better comfort, current disposable absorbent articles are typically provided with a topsheet that is flexible, soft feeling, and non-irritating to the wearer's skin.

Regarding comfort, some consumers may desire a product that has sufficient thickness and stiffness to provide the desirable amount of protection while also being flexible. Lofty materials may be utilized to provide a cushiony feeling article.

Disposable absorbent articles are generally designed to comprise a liquid pervious topsheet, a liquid impervious backsheet and an absorbent core disposed between the topsheet and the backsheet. So as not to prevent liquid transfer from a topsheet to an absorbent core and minimize an amount of body fluid remaining on the topsheet, absorbent articles have been designed by incorporating a fluid management layer between a topsheet and an absorbent core. One desirable function of a fluid management layer is to quickly acquire liquids or other bodily exudates and transfer them to the absorbent core in an efficient manner Another one is to reduce fluid amount in the topsheet to avoid a wetness sensory. To reduce the liquid amount in a topsheet, a fluid management layer is required to have a good wicking property to distribute the liquid along a planar direction of the fluid management layer to lower the liquid concentration at the loading point and a high capillary force to suck the liquid from a topsheet. Both a wicking property and a capillary force are contributed by small pore sizes either in a planar direction or a z-direction. While small size pores in a fluid management layer enhances wicking property and capillary force, it brings high flow resistance for the liquid to penetrate the fluid management layer, which results in a slow acquisition speed. Therefore, there is typically a tradeoff between acquisition speed and rewet. Namely, the quicker the acquisition speed, the higher the rewet tends to increase and vice versa.

US2020/0315872A discloses a fluid management layer comprising 10 percent to 60 percent by weight absorbent fibers, from 15 percent to 70 percent of resilient fibers, and 25 percent to 70 percent stiffening fibers. However, absorbent fibers tend to swell when exposed to liquid which may result in smaller pore size and blocking some channels in the fluid management layer and eventually negatively impacts acquisition time and/or rewet.

As such there is a need to create an absorbent article with improved fluid acquisition and rewet.

As such there is a need to create an absorbent article that accounts for the possible tradeoffs such that it is both comfortable while maintaining performance.

SUMMARY OF THE INVENTION

The present invention relates to a nonwoven sheet comprising from about 10% to about 60% of non-swelling wicking fibers by weight of the fluid management layer, from about 15% to about 70% of resilient fibers by weight of the fluid management layer, and from about 25% to about 70% of stiffening fibers by weight of fluid management layer as determined by the Material Composition Analysis, and wherein the non-swelling wicking fibers has a relative shape factor in radius in the range of about 25% to about 100% as determined the Relative Shape Factor in Radius Test, and a linear density of 0.8 dtex to 3.3 dtex as determined the Fiber Decitex Test.

The present invention relates to a nonwoven sheet comprising from about 10% to about 60% of non-swelling wicking fibers by weight of the fluid management layer, and at least of from about 15% to about 70% of resilient fibers and from about 25% to about 70% of stiffening fibers by weight of fluid management layer as determined by the Material Composition Analysis, and wherein the non-swelling wicking fibers has a relative shape factor in radius in the range of about 25% to about 100% as determined the Relative Shape Factor in Radius Test, and a linear density of 0.8 dtex to 3.3 dtex as determined the Fiber Decitex Test.

The present invention also relates to an absorbent article comprising a liquid permeable topsheet, a liquid impermeable backsheet, an absorbent core disposed between the topsheet and the backsheet, and a fluid management layer disposed between the topsheet and the absorbent core, the liquid management layer comprising a nonwoven, wherein the nonwoven comprises comprising from about 10% to about 60% of non-swelling wicking fibers by weight of the fluid management layer, from about 15% to about 70% of resilient fibers by weight of the fluid management layer, and from about 25% to about 70% of stiffening fibers by weight of fluid management layer as determined by the Material Composition Analysis, and wherein the non-swelling wicking fibers has a relative shape factor in radius in the range of about 25% to about 100% as determined the Relative Shape Factor in Radius Test, and a linear density of 0.8 dtex to 3.3 dtex as determined the Fiber Decitex Test.

The present invention also relates to an absorbent article comprising a liquid permeable topsheet, a liquid impermeable backsheet, an absorbent core disposed between the topsheet and the backsheet, and a fluid management layer disposed between the topsheet and the absorbent core, the liquid management layer comprising a nonwoven, wherein the nonwoven comprises comprising from about 10% to about 60% of non-swelling wicking fibers by weight of the fluid management layer, and at least one of from about 15% to about 70% of resilient fibers and from about 25% to about 70% of stiffening fibers by weight of fluid management layer as determined by the Material Composition Analysis, and wherein the non-swelling wicking fibers has a relative shape factor in radius in the range of about 25% to about 100% as determined the Relative Shape Factor in Radius Test, and a linear density of 0.8 dtex to 3.3 dtex as determined the Fiber Decitex Test.

For ease of discussion, the absorbent article will be discussed with reference to the numerals referred to in these figures. The figures and detailed description should however not be considered limiting the scope of the claims, unless explicitly indicated otherwise, and the invention disclosed herein is also used in a wide variety of absorbent article forms.

BRIEF DESCRIPTION OF THE DRAWINGS

In the drawings, like numerals or other designations designate like features throughout the views. Some of the figures may have been simplified by the omission of selected elements for the purpose of more clearly showing other elements. None of the drawings are necessarily to scale.

DETAILED DESCRIPTION

Figure 1:
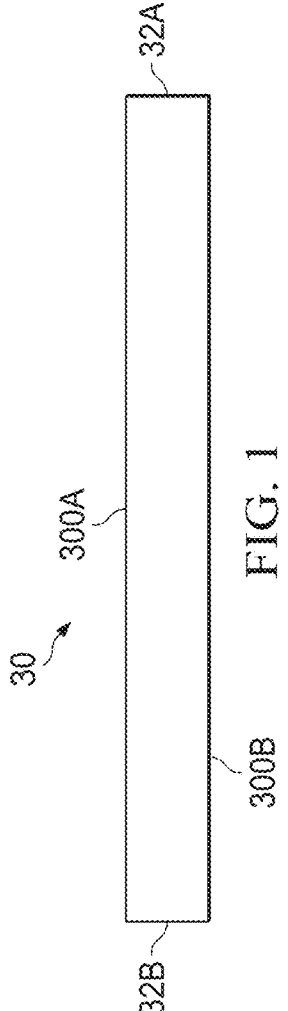
FIG. 1 is a schematic representation of an elevation view of a fluid management layer according to the present invention.

As used herein, the following terms shall have the meaning specified thereafter: "Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments (e.g., liners, pads and briefs) and/or feminine hygiene products.

The term "integrated" as used herein is used to describe fibers of a nonwoven material which have been intertwined, entangled, and/or pushed/pulled in a positive and/or negative Z-direction (direction of the thickness of the nonwoven material). Some exemplary processes for integrating fibers of a nonwoven web include spunlacing and needlepunching. Spunlacing uses a plurality of high pressure water jets to entangle fibers. Needlepunching involves the use of needles to push and/or pull fibers to entangle them with other fibers in the nonwoven.

The term "carded" as used herein is used to describe structural features of the fluid management layers described herein. A nonwoven utilizes fibers which are cut to a specific length, otherwise known as "staple length fibers." Staple length fibers may be any suitable length. For example, staple length fibers may have a length of up to 120 mm or may have a length as short as 10 mm. However, if a particular group of fibers are staple length fibers, for example viscose fibers, then the length of each of the viscose fibers in the nonwoven is predominantly the same, i.e. the staple length. It is worth noting that where additional staple fiber length fiber types are included, for example, polypropylene fibers, the length of each of the polypropylene fibers in the nonwoven is also predominantly the same.

In contrast, continuous filaments such as by spunbonding or meltblowing processes, do not create staple length fibers. Instead, these filaments are of an indeterminate length and are not cut to a specific length as noted regarding their staple fiber length counterparts.

The "longitudinal" direction is a direction running parallel to the maximum linear dimension, typically the longitudinal axis, of the article and includes directions within 45° of the longitudinal direction. "Length" of the article or component thereof, when used herein, generally refers to the size/distance of the maximum linear dimension, or typically to the size/distance of the longitudinal axis, of an article or part thereof.

The "lateral" or "transverse" direction is orthogonal to the longitudinal direction, i.e. in the same plane of the majority of the article and the longitudinal axis, and the transverse direction is parallel to the transverse axis. "Width" of the article or of a component thereof, when used herein, refers to the size/distance of the dimension orthogonal to the longitudinal direction of the article or component thereof, i.e. orthogonal to the length of the article or component thereof, and typically it refers to the distance/size of the dimension parallel of the transverse axis of the article or component.

The "Z-direction" is orthogonal to both the longitudinal and transverse directions.

"Machine Direction" or "MD" as used herein means the direction parallel to the flow of the nonwoven through the nonwoven making machine and/or absorbent article product manufacturing equipment.

"Cross Machine Direction" or "CD" as used herein means the direction parallel to the width of the nonwoven making machine and/or absorbent article product manufacturing equipment and perpendicular to the machine direction.

A nonwoven sheet as disclosed herein can be used in a variety of disposable absorbent articles, but is particularly useful in diapers, feminine hygiene products and incontinence products such as sanitary napkins and incontinence pads. The nonwovens of the present disclosure can be particularly effective as a fluid management layer in the above absorbent articles. Additionally, the nonwoven of the present disclosure provides increased caliper, even at lower basis weights, and has good fluid handling properties both in an acquisition speed and rewet mitigation.

The fluid management layer of the present disclosure maybe arranged between a topsheet an absorbent core.

The fluid management layer of the present disclosure may comprise one or more nonwoven webs or nonwoven layers (herein after, "nonwoven web" or "nonwoven webs", collectively). The one or more nonwoven webs may be carded nonwoven webs.

Fibers of the nonwoven web may be integrated. Fibers of the nonwoven web may thermo-bonded. Where at least two nonwoven webs are utilized, fibers in each web of the at least two webs may be integrated. Where at least two nonwoven webs are utilized, fibers of the at least two webs may be integrated. Alternatively, the at least two nonwoven webs may be attached to one another by, for example, thermal bonding, adhesive bonding or a combination thereof. In one embodiment, fibers of the nonwoven of the present invention are integrated. In one embodiment, the nonwoven of the present invention is spunlaced.

A wide variety of configurations for a fluid management layer may be achieved. However, it is important that the fluid management layer of the present disclosure have adequate openness to allow for quick acquisition of fluid, yet also be able to lock away liquid insults to reduce the likelihood of rewet even upon repeated liquid insults. With this in mind, the nonwoven webs which make up the fluid management layer may be different from one another. For example, one of the nonwoven webs may comprise a different fiber blend than the others. In one embodiment, assuming the first nonwoven web would be closest to the wearer-facing surface in an absorbent article, the fiber selection for a first nonwoven web may be such that there is more openness associated with this web. A second nonwoven web may be similarly configured, or may be configured to collect liquid insults from the void space of the first nonwoven webs and effectively distribute these liquid insults to an absorbent core. In another embodiment, a first nonwoven web may be such that there is more openness associated with this web. A second nonwoven web may be similarly configured. In contrast, a third nonwoven web may be configured to collect liquid insults from the void space of the first and second nonwoven webs and effectively distribute these liquid insults to an absorbent core. Alternatively, the first nonwoven web and the second nonwoven web may be configured the same.

Where a fiber makeup of one of the nonwoven webs is different than a fiber makeup of another nonwoven web, the nonwoven is a heterogenous configuration. Alternatively, where the nonwoven webs having the same fiber makeup is termed a homogeneous configuration.

When the nonwoven web(s) are integrated, they cannot be manually separated—at least not without substantial effort and time. Each nonwoven web forms a stratum in the overall fluid management layer. Each stratum can maintain its unique properties for at least a portion of the stratum along the z-direction, even when integrated into a larger fluid management layer. The fluid management layer can provide capillary suction to "pull" fluid through the topsheet, which is competing for trickle/low flow conditions. The fluid management layer also can contain a gush by providing distribution functions to efficiently utilize the absorbent core, as well as provide intermediate storage until the absorbent core can accept fluid.

As noted previously, absorbent articles which exhibit a soft cushiony feel and fluid handling characteristics is in accordance with the present disclosure. Absorbent articles of the present disclosure may also have good resilience. Notably, typical calipers of webs from conventional spunlace lines achieve a caliper factor (caliper per 10 gsm of basis weight) of 0.03 to 0.12. In contrast, the fluid management layers of the present disclosure can exhibit a caliper factor of at least 0.13 mm, or at least about 0.15 mm, or about 0.2 mm, including any values within these ranges and any ranges created thereby. The fluid management layer of the present disclosure can have a caliper factor of between 0.13 mm to about 0.3 mm, or from about 0.14 mm to about 0.25 mm, or from about 0.15 mm to about 0.22 mm, including all values within these ranges and any ranges created thereby. The caliper and caliper factor of the fluid management layers of the present disclosure may be determined by the Caliper and Caliper Factor test methods disclosed herein.

Regardless of whether the fluid management layer is utilized in an adult incontinence article menstrual article, liner, or other hygiene article, of importance is the ability of the fluid management layer to acquire liquid insults from the topsheet and to pull the liquid far enough from the topsheet, such that the topsheet does not feel wet. To accomplish this, increased caliper factor of the fluid management layer discussed herein can facilitate fluid acquisition due to the increased void volume of the fluid management layer. The higher caliper at the lower basis weight equals more void volume with higher permeability. Additionally, the increased caliper of the fluid management layer can also provide a stain masking benefit. Namely, the stains that are visible through the topsheet with absorbent articles using the fluid management layer of the present disclosure, appear much smaller than their conventional fluid management layer counterparts.

The fluid management layer of the present disclosure can have a basis weight of up to 120 grams per square meter (gsm), of up to 100 gsm; or between about 20 gsm to about 120 gsm; or between about 30 gsm to about 100 gsm, or between from about 45 gsm to about 80 gsm, and or between about 50 gsm to about 65 gsm, including any values within these ranges and any ranges created thereby. Some absorbent articles may not require as much basis weight as recited above. For example, liners which generally do not have the same level of absorbent capacity as menstrual pads may be able to have a reduced basis weight over that which was recited above. For example, the fluid management layer may have a basis weight of between 20 gsm to 70 gsm or between 35 gsm to about 65 gsm, or from about 30 gsm to about 55 gsm, specifically including all values within these ranges and any ranges created thereby.

In one embodiment, the fluid management layer is spunlaced that is produced via conventional spunlace processes widely known in the industry. In such a case, it is also worth noting that due to the fiber integration, the fluid management layer may not require adhesives or latex binders for stability. Additionally, the nonwoven of the fluid management layer can be manufactured from an assortment of suitable fiber types that produce the desired performance characteristics.

As will be discussed in additional detail below, the types of fibers in the fluid management layer of the present disclosure are described in terms of their functionality within the fluid management layer. For example, non-swelling wicking fibers are utilized to distribute liquid via channels in the surface of fibers due to a high relative shape factor in radius. Non-swelling wicking fibers do not absorb liquid and do not swell when exposed to liquid, so that the fluid management layer can maintain channels and pores upon fluid insults and eventually can maintain fluid acquisition speed. Stiffening fibers are utilized to bond together via heat treatment thereby providing stiffness and resiliency to the fluid management layer. Resilient fibers are utilized to provide recovery from compressive forces which act against the fluid management layer. Optional absorbent fibers may be utilized to absorb liquid insults.

In order to enhance the stabilizing effect of the integration, crimped fibers may be utilized. One or more of the non-swelling wicking fibers, stiffening fibers, and resilient fibers may be crimped prior to integration. For example, where synthetic fibers are utilized, these fibers may be mechanically crimped via intermeshing teeth.

The fluid management layer of the present disclosure comprises from about 10 percent to about 60 percent, or from about 15 percent to about 50 percent, or from about 20 percent to about 40 percent by weight of non-swelling wicking fibers, specifically reciting all values within these ranges and any ranges created thereby.

Additionally, the fluid management layer also comprises sufficient weight percentage of resilient fibers which impact the recovery of the absorbent article from compressive loads experienced during use. The fluid management layer of the present disclosure comprises from about 15 percent to about 70 percent, or from about 20 percent to about 60 percent, or from about 25 percent to about 50 percent by weight of resilient fibers, specifically reciting all values within these ranges and any ranges created thereby.

Moreover, stiffening fibers may be utilized to help the fluid management layer of the present disclosure provide resiliency to the absorbent article. For example, as discussed hereafter, stiffening fibers may be bonded to one another via heat treatment of the fluid management layer during production. This bonding of the stiffening fibers creates a support matrix which helps with resiliency and stiffness of the fluid management layer. With this in mind, the fluid management layer comprises from about 25 percent to about 70 percent, or from about 30 percent to about 60 percent, or from about 40 percent to about 55 percent of stiffening fiber, specifically reciting all values within these ranges and any ranges created thereby.

Where caliper, resiliency, and a soft cushiony feel are the objective, the weight percentage of stiffening fibers may be greater than or equal to the weight percentage of resilient fibers. The weight percentages non-swelling wicking fibers, resilient fibers and stiffening fibers can be determined depending on product design purposes.

A ratio of non-swelling wicking fibers in the fluid management layers of the present disclosure to stiffening fibers by weight percentage can be from about 1:7 to about 2:1, or from about 1:4 to about 1.5:1, or from about 1:2 to about 1:1, specifically reciting all values within these ranges and any ranges created thereby Similarly a ratio of non-swelling wicking fibers to resilient fibers by weight percentage can be from about 1:7 to about 3:1, or from about 1:2 to about 2:1, or from about 1:1.5 to about 1:1, specifically reciting all values within these ranges and any ranges created thereby.

With the above in mind, the inventors have also surprisingly discovered that careful selection of the fiber types in the fluid management layer and the linear densities of the fiber types can achieve the desired outcome of quick acquisition and mitigated rewet even with repeated fluid insults. The fiber types of the fluid management layer, and the individual strata in case the fluid management layer comprises at least strata are discussed in additional detail hereafter. It is worth noting that the discussion below regarding fiber types in the strata of the fluid management layer assumes that the first nonwoven web is nearer to the topsheet than the web(s) of the additional card(s) when the fluid management layer has more than one nonwoven web.

The non-swelling wicking fibers can help fluid distribution especially in X-Y direction perpendicular to the z-direction. The non-swelling wicking fibers do not absorb liquid and do not swell when exposed to liquid, so that the fluid management layer can maintain channels and pores upon fluid insults and eventually can maintain fluid acquisition speed. The non-swelling wicking fibers can be any suitable synthetic thermoplastic fibers having a linear density in the range of from about 0.8 dtex to about 3.3 dtex such as monocomponent fibers including polypropylene ("PP"), polyethylene terephthalate ("PET"), polybutylene terephthalate ("PBT"), and bicomponent fibers comprising polyolefin resins, and other suitable thermoplastic fibers known in the art. Some suitable linear density values of non-swelling wicking fibers for use in the fluid management layers of the present disclosure may range from about 0.8 dtex to about 3.3 dtex, or from about 1.2 dtex to about 2.5 dtex, or from about 1.5 dtex to about 2 dtex, specifically reciting all values within these ranges and any ranges created thereby. The decitex (dtex) values for the non-swelling wicking fibers, stiffening fibers and/or resilient fibers may be determined via the Fiber Decitex method disclosed herein.

The non-swelling wicking fibers for the fluid management layer have a high relative shape factor in radius ("RSFR") in the range of about 25% to about 100%, or in the range of about 25% to about 80%, or in the range of about 30% to about 80%, as determined via the Relative Shape Factor in Radius test disclosed herein. Fibers having high RSFR value are considered having deep channels along the fibers, so that nonwoven containing the fibers can have high wicking power. In that point, an upper limit of the RSFR may not be critical. Fibers having too low RSFR values are not suitable as non-swelling wicking fibers as such fibers have swallow channels along the fibers, so that nonwoven containing the fibers may not have wicking power in a desirable level. Some examples of non-swelling wicking fibers may have cross sections such as cross, trilobal, pentagonal, "H," "Y," "X," "T," or flat ribbon. Each stratum may comprise a different percentage of non-swelling wicking fibers by weigh to the stratum weight.

As noted previously, in addition to non-swelling wicking fibers, the fluid management layer of the present disclosure comprises stiffening fibers. Stiffening fibers may be utilized to help provide structural integrity to the fluid management layer. The stiffening fibers can help increase structural integrity of the fluid management layer in a machine direction and/or in a cross-machine direction which can facilitate web manipulation during processing of the fluid management layer for incorporation into a disposable absorbent article.

Some suitable linear density values of stiffening fiber are provided. For example, the stiffening fiber linear density may range from about 1.0 dtex to about 6 dtex, or from about 1.5 dtex to about 5 dtex, or from about 2.0 dtex to about 4 dtex, specifically reciting all values within these ranges and any ranges created thereby.

Some examples of suitable stiffening fibers include bicomponent fibers comprising polyolefins. In some embodiments, bi-component fibers suitable for the stiffening fibers may comprises polyethylene and polyethylene terephthalate components or polyethylene terephthalate and co-polyethylene terephthalate components. The components of the bi-component fiber may be arranged in a core sheath arrangement, a side by side arrangement, an eccentric core sheath arrangement, a trilobal arrangement, or the like. In one specific example, the stiffening fibers may comprise bi-component fibers having polyethylene/polyethylene terephthalate components arranged in a concentric, core—sheath arrangement where the polyethylene is the sheath.

While other materials may be useful, the stiffness of polyethylene terephthalate is useful in creating a resilient structure. In contrast, the polyethylene component of the stiffening fibers can be utilized to bond to one another during heat treatment. This can help provide tensile strength to the web in both the MD and CD. Additionally, the bonding of the polyethylene component to other polyethylene components of stiffening fibers can create fixed points in the nonwoven. These fixed points can reduce the amount of fiber-to-fiber sliding which can increase the resiliency of the material.

One of the benefits of the stiffening fibers is that the integrated nonwoven may be heat treated post fiber entanglement. The heat treatment can provide additional structural integrity to the integrated nonwoven by forming bonds between adjacent stiffening fibers. So, where there is a higher percentage of stiffening fibers, more connection points may be created. Too many connection points can yield a much stiffer fluid management layer which may negatively impact comfort. As such, the weight percentage of the stiffening fibers is of critical importance when designing an absorbent article.

Regarding the heat stiffening process, any suitable temperature may be utilized. And, the suitable temperature may be impacted, in part, by the constituent chemistry of the stiffening fibers as well as by the processing fluid management layer web. For example, the fluid management layer web may be heat stiffened at a temperature of 132 degrees Celsius. However, it is also worth noting, that in order to provide a uniform stiffness property across the fluid management layer, any heating operation should be set up to provide uniform heating to the fluid management layer web. Even small variations in temperature can greatly impact the tensile strength of the fluid management layer.

The fluid management layer of the present disclosure further comprises resilient fibers. The resilient fibers can help the fluid management layer maintain its permeability and compression recovery. Any suitable size fiber may be utilized. For example, the resilient fibers can have a linear density of about 6 dtex to about 15 dtex, or from about 7 dtex to about 12 dtex, or from about 7 dtex to about 10 dtex, especially when the resilient fibers are multicomponent fibers such as bicomponent fibers. The resilient fibers can have a linear density of about 4 dtex to about 15 dtex, or from about 7 dtex to about 12 dtex, or from about 7 dtex to about 10 dtex, especially when the resilient fibers are monocompenent fibers such as PP, PET and PBT. Fibers with a small liner density may not provide desirable resilience to the nonwoven. In another specific example, the fluid management layer may comprise resilient fibers having variable cross sections, e.g. round and hollow spiral, and/or may comprise resilient fibers having variable dtex's. In such forms, the resilient fibers may be hollow spiral.

The resilient fibers can be any suitable thermoplastic fiber, such as polypropylene (PP), polyethylene terephthalate, or other suitable thermoplastic fibers known in the art. The length of the resilient fibers can be in the range of about 20 mm to about 100 mm, or about 30 mm to about 50 mm or about 35 mm to about 45 mm. The thermoplastic fibers can have any suitable structure or shape. For example, the thermoplastic fibers can be round or have other shapes, such as spiral, scalloped oval, trilobal, scalloped ribbon, and so forth. Further, the PP fibers can be solid, hollow or multi-hollow. The resilient fibers may be solid and round in shape. Other suitable examples of resilient fibers include polyester/co-extruded polyester fibers. Additionally, other suitable examples of resilient fibers include bi-component fibers such as polyethylene/polypropylene, polyethylene/polyethylene terephthalate, polypropylene/polyethylene terephthalate. These bi-component fibers may be configured as a sheath and a core. The bi-component fibers may provide a cost-effective way to increase basis weight of the material while additionally enabling optimization of the pore size distribution.

The resilient fibers can be polyethylene terephthalate (PET) fibers, or other suitable non-cellulosic fibers known in the art. The PET fibers can have any suitable structure or shape. For example, the PET fibers can be round or have other shapes, such as spiral, scalloped oval, trilobal, scalloped ribbon, hollow spiral, and so forth. Further, the PET fibers can be solid, hollow or multi-hollow. In one particular example, fibers may be fibers made of hollow/spiral PET. Optionally, the resilient fibers may be spiral-crimped or flat-crimped. The resilient fibers may have a crimp value of between about 4 and about 12 crimps per inch (cpi), or between about 4 and about 8 cpi, or between about 5 and about 7 cpi, or between about 9 and about 10 cpi. Particular non-limiting examples of resilient fibers can be obtained from Wellman, Inc. Ireland under the trade names H1311 and T5974. Other examples of suitable resilient fibers for utilization in the carded staple-fiber nonwovens detailed herein are disclosed in U.S. Pat. No. 7,767,598 to Schneider et al.

It is worth noting that the stiffening fibers and resilient fibers should be carefully selected. For example, while the constituent chemistries of the stiffening fibers and the resilient fibers may be similar, resilient fibers should be selected such that their constituent material's melting temperature is higher than that of the stiffening fibers. Otherwise, during heat treatment, resilient fibers would bond to stiffening fibers and vice versa and could create an overly rigid structure.

Without wishing to be bound by theory, when the fluid management layer includes absorbent fibers, it is believed that for weight percentage of absorbent fibers above about 30 percent, within the gsm ranges disclosed herein, the resilient fibers and/or stiffening fibers should be carefully selected. Where a soft, cushiony fluid management layer with a caliper factor of at least 0.13 or greater as described herein, the resilient and/or stiffening fibers can be selected to counteract the loss of structural integrity of the absorbent fibers when wet. For example, a higher dtex of resilient fiber may be beneficial in counteracting the loss of integrity experienced by the absorbent fibers. In such instances, resilient fibers may be utilized having a dtex of between about 5 dtex to about 15 dtex, or from about 6 dtex to about 12 dtex, or from about 7 dtex to about 10 dtex.

In addition to or an alternative thereof, the stiffening fibers may be configured to provide greater structural integrity. For example, the stiffening fibers may comprise bicomponent fibers in a core-sheath configuration where the sheath is co-polyethylene terephthalate. However, with such a material change, additional problems may occur. For example, the joining of materials to the fluid management layer may then only be via adhesive as opposed to fusion bonding.

Where the absorbent fibers make up 30 percent by weight or more. In such instances, the linear density of the stiffening fibers may be from about 3 dtex to about 6 dtex, or from about 4 dtex to about 6 dtex.

The fluid management layer of the present disclosure may further comprise absorbent fibers. Absorbent fibers can provide absorption of liquid insults from the wearer-facing surface or topsheet. However, when absorbent fibers absorb liquid, they tend to lose some of their structural integrity. The loss of structural integrity can reduce the resiliency of the absorbent article and lead to increased bunching and increased leakage. Accordingly, while in principle, a large percentage of absorbent fibers is good for draining liquid insults from the wearer-facing surface and/or topsheet rapidly, the large percentage will lead to other problems with the absorbent article as mentioned heretofore.

In light of the potential problems associated with having too much of a weight percentage of absorbent fibers, the fluid management layer of the present disclosure may comprise from about 1 percent to about 40 percent by weight, or from about from about 5 percent to about 35 percent by weight, or from about 1 percent to about 20 percent by weight, specifically including any values within these ranges and any ranges created thereby of absorbent fibers.

The absorbent fibers of the fluid management layer may have any suitable shape. Some examples include trilobal, "H," "Y," "X," "T," round, or flat ribbon. Further, the absorbing fibers can be solid, hollow or multi-hollow.

Any suitable absorbent material for the absorbent fibers may be utilized. Some examples of absorbent materials include cotton, pulp, rayon or regenerated cellulose or combinations thereof. In one example, the fluid management layer may comprise viscose cellulose fibers. The length of the absorbent fibers can be in the range of about 20 mm to about 100 mm, or about 30 mm to about 50 mm or about 35 mm to about 45 mm, specifically reciting all values within these ranges and any ranges created thereby. In general, the fiber length of pulp is from about 4 to 6 mm and cannot used in conventional carding machines because the pulp fibers are too short. So, if pulp is desired as a fiber in the fluid management layer, then additional processing to add pulp to the nonwoven webs may be required. As an example, pulp may be airlaid between nonwoven webs with the combination being subsequently integrated. As another example, tissue may be utilized in combination with the nonwoven webs and the combination may be subsequently integrated.

A schematic representation of an exemplary fluid management layer in accordance with the present disclosure is provided in FIG. 1. As shown, the fluid management layer 30 comprises the first surface 300A, the opposing second surface 300B, and opposing end edges 32A and 32B. Between the first surface 300A and the second surface 300B, the fluid distribution layer 30 comprises at least one stratum, or at least two or more strata along the Z-direction.

Figure 2:
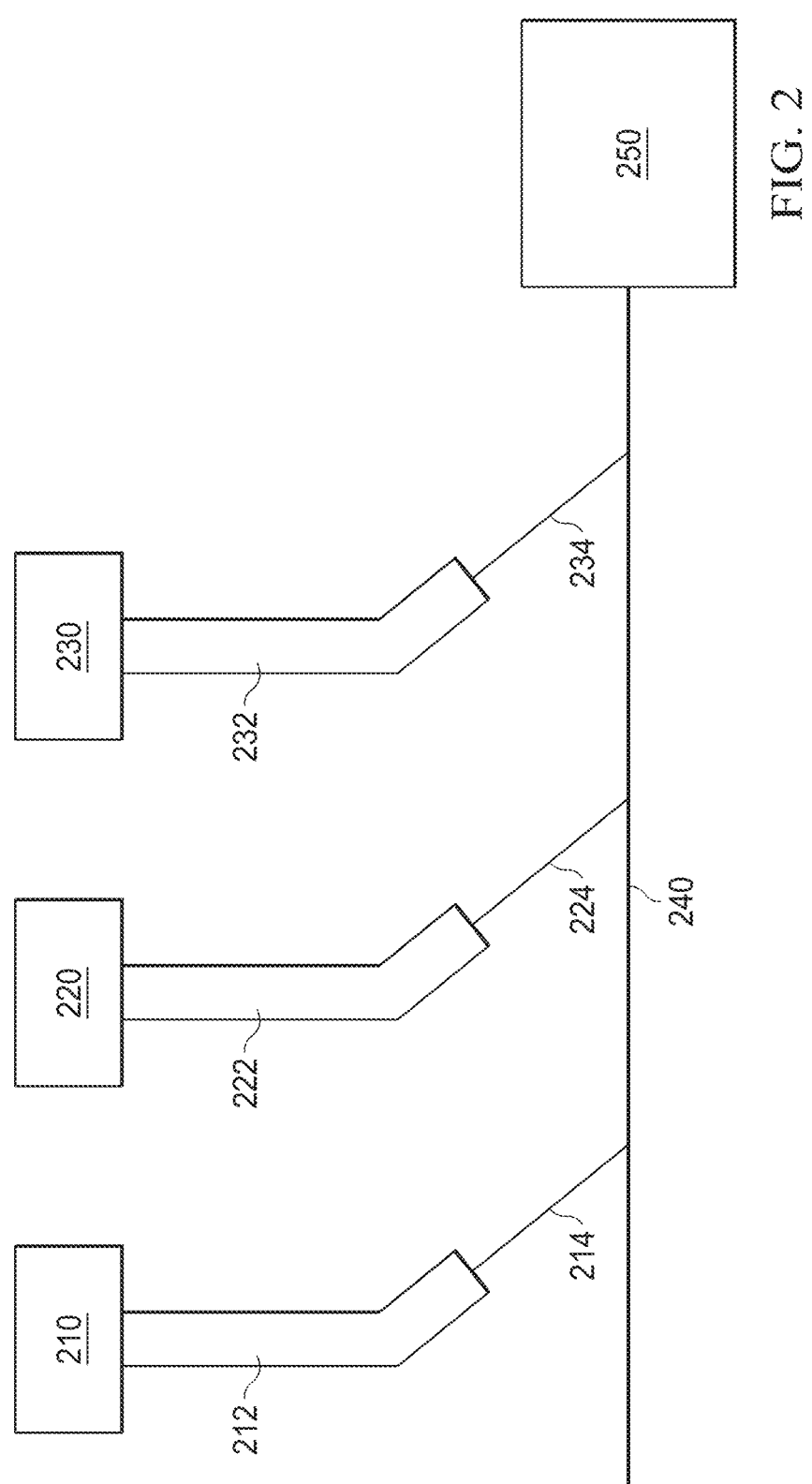
FIG. 2 is a schematic representation of a process which can be utilized to construct fluid management layer according to the present invention.

An exemplary process for forming the fluid management layer of the present disclosure is shown in FIG. 2. As shown, a plurality of carding machines 210, 220, and 230 may each create a nonwoven web, e.g. 214, 224, and 234, respectively, which is transferred to a carrier belt 240. Each of the nonwoven webs 214, 224, and 234, may be provided to the carrier belt 240 via a web chute 212, 222, 232, respectively. It is also worth noting that after the nonwoven 214 is deposited on the carrier belt 240, the nonwoven 224 is then deposited on the first nonwoven 214 on the carrier belt 240. Similarly, the third nonwoven web 234 deposited on the second nonwoven 224 and the first nonwoven 214 on the carrier belt 240. Subsequently, each of the first, second, and third nonwoven webs 214, 224, and 234 are then provided to an integration process 250 which utilizes either needles and/or high-pressure water streams to entangle the fibers of the first, second, and third nonwoven webs. Both carding and integration processes are well known in the art.

Additional carding machines may be utilized. Additionally, the fluid management layer of the present disclosure may be produced utilizing only two out of the three cards. In such instances, the first nonwoven web 214 would be deposited on the carrier belt 240. And, subsequently, the second nonwoven web 224 would be deposited on the first nonwoven web 214. Then, the first nonwoven web 214 and the second nonwoven web 224 would be integrated as described herein.

It is worth noting that with the arrangement provided in schematic diagram of FIG. 2, a wide variety of configurations for a fluid management layer may be achieved. However, it is important that the fluid management layer of the present disclosure have adequate openness to allow for quick acquisition of fluid yet also are able to lock away liquid insults to reduce the likelihood of rewet. With this in mind, the nonwoven webs, i.e. 214, 224, and/or 234, may be different from one another. For example, one of the nonwoven webs may comprise a different fiber blend than the others. Specifically, assuming the first nonwoven web would be closest to the wearer-facing surface in an absorbent article, the fiber selection for the first nonwoven web 214 may be such that there is more openness associated with this web. The second nonwoven web 224 may be similarly configured. In contrast, the third nonwoven web 234 may be configured collect liquid insults from the void space of the first and second nonwoven webs 214 and 224 and effectively distribute these liquid insults to an absorbent core. Alternatively, the first nonwoven web 214, the second nonwoven web 224 and the third nonwoven web 234 may be configured the same.

The fluid management layer of the present disclosure may be incorporated into a variety of absorbent articles.

Absorbent Articles

Figure 3A:
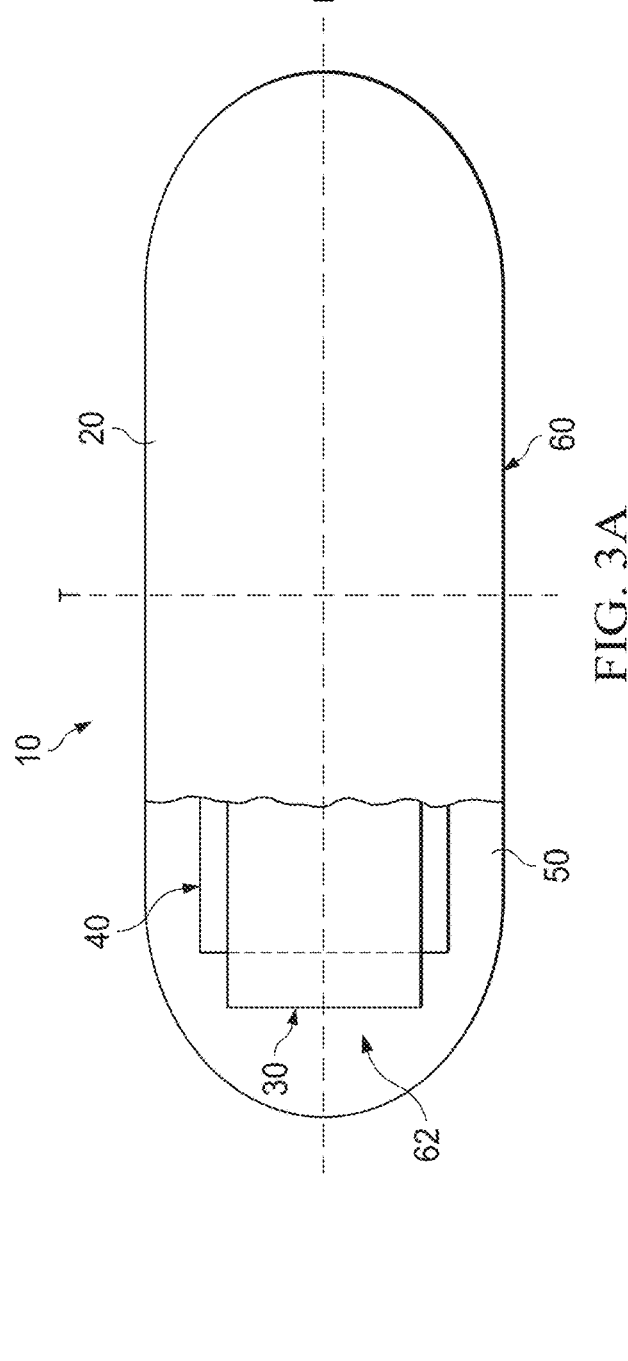
FIG. 3A is a schematic representation of a disposable absorbent article according to the present invention.

An exemplary schematic showing an absorbent article, i.e. a feminine hygiene pad, of the present disclosure is shown in FIG. 3A. As shown, absorbent articles 10 in accordance with the present disclosure comprise a topsheet 20, a backsheet 50, and an absorbent core 40 disposed between the topsheet 20 and the backsheet 50. A fluid management layer 30 is disposed between the topsheet 20 and the absorbent core 40. The absorbent article has a wearer-facing surface 60 and an opposing garment-facing surface 62. The wearer-facing surface 60 primarily comprises the topsheet 20 while the garment-facing surface 62 primarily comprises the backsheet 50. Additional components may be included in either the wearer-facing surface 60 and/or the garment-facing surface 62. For example, where the absorbent article is an incontinent pad, a pair of barrier cuffs which extend generally parallel to a longitudinal axis L of the absorbent article 10, may also form a portion of the wearer-facing surface 60. Similarly, a fastening adhesive may be present on the backsheet 50 and form a portion of the garment-facing surface 62 of the absorbent article.

Figure 3B:
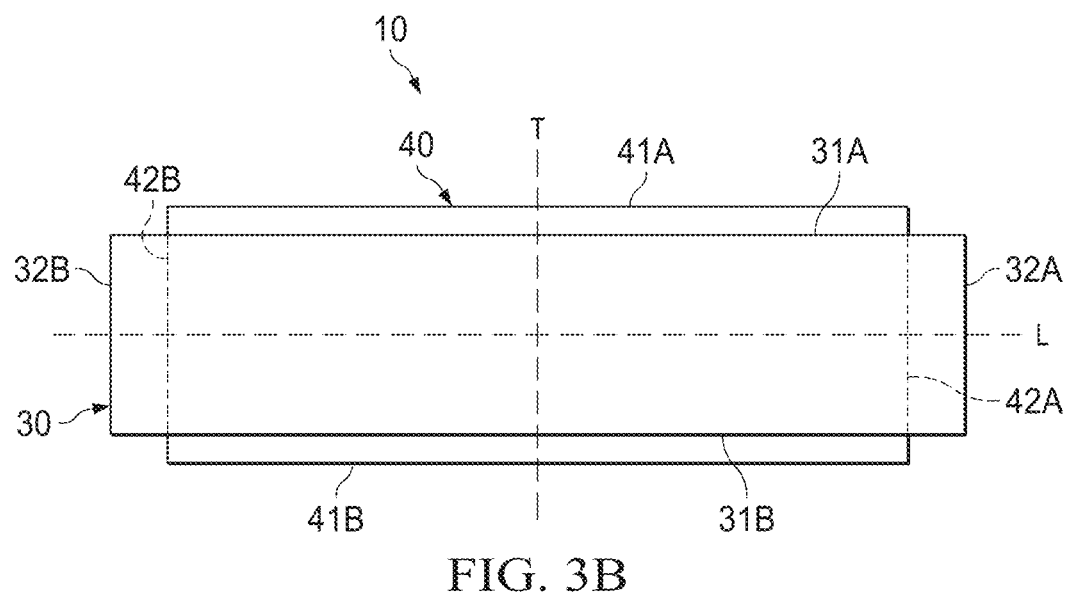
FIG. 3B is a schematic representation of an absorbent system of the disposable absorbent article shown in FIG. 3A.

An exemplary configuration for the fluid management layer of the present disclosure is shown in FIG. 3B. As shown, the fluid management layer 30 comprises opposing end edges 32A and 32B which may extend generally parallel to a transverse axis T. And, the fluid management layer 30 comprises side edges 31A and 32B which may extend generally parallel to the longitudinal axis L. Similarly, the absorbent core 40 comprises opposing end edges 42A and 42B which may extend generally parallel to the transverse axis T. And, the absorbent core 40 may comprise side edges 41A and 41B which extend generally parallel to the longitudinal axis L.

As shown, each of the end edges 32A and 32B of the fluid management layer 30 may be disposed longitudinally outboard of the absorbent core 40. However, this is not necessarily required. For example, the end edges 32A and/or 32B may be coextensive with the absorbent core 40 or the end edges 32A and/or 32B may be disposed longitudinally inboard of the end edges 42A and/or 42B of the absorbent core 40.

Similarly, the side edges 31A and/or 31B may be disposed transversely outboard of the side edges 41A and/or 41B of the absorbent core 40. Or, the side edges 31A and/or 31B may be coextensive with the side edges 41A and/or 41B of the absorbent core 40. Additionally, the end edges and/or side edges of the absorbent core and/or fluid management layer may be curvilinear in nature. For example, the side edges of the absorbent core and/or the fluid management layer may curve inward from the ends toward the transverse axis. Such construction may help with conformity of the absorbent article. Similarly, the end edges in conjunction with or independently of the side edges of the absorbent core and/or fluid management layer may comprise a curvilinear path which is either generally concave or generally convex.

Referring to FIGS. 3A and 3B again, the topsheet 20 may be joined to the backsheet 50 by attachment methods (not shown) such as those well known in the art. The topsheet 20 and the backsheet 50 may be joined directly to each other in the article periphery and may be indirectly joined together by directly joining them to the absorbent core 40, the fluid management layer 30, and/or additional layers disposed between the topsheet 20 and the backsheet 50. This indirect or direct joining may be accomplished by attachment methods which are well known in the art.

The topsheet 20 may be compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, may also provide for the transfer or migration of the lotion composition onto an external or internal portion of a wearer's skin.

A suitable topsheet 20 can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet.

Nonlimiting examples of woven and nonwoven materials suitable for use as the topsheet include fibrous materials made from natural fibers, e.g. cotton, including 100 percent organic cotton, modified natural fibers, synthetic fibers, or combinations thereof. These fibrous materials can be either hydrophilic or hydrophobic, but it is preferable that the topsheet be hydrophobic or rendered hydrophobic. As an option, portions of the topsheet can be rendered hydrophilic, by the use of any known method for making topsheets containing hydrophilic components. Nonwoven fibrous topsheets 20 may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The topsheet 20 may be formed from a combination of an apertured film and a nonwoven. For example, a film web and a nonwoven web can be combined as described in U.S. Pat. No. 9,700,463. Alternatively, a film may be extruded onto a nonwoven material which is believed to provide enhanced contact between the film layer and the nonwoven material.

The backsheet 50 may be positioned adjacent a garment-facing surface of the absorbent core 40 and may be joined thereto by attachment methods such as those well known in the art. For example, the backsheet 50 may be secured to the absorbent core 40 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art.

The backsheet 50 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 50 may prevent, or at least inhibit, the exudates absorbed and contained in the absorbent core 40 from wetting articles of clothing which contact the absorbent article 10 such as undergarments. However, the backsheet 50 may permit vapors to escape from the absorbent core 40 (i.e., is breathable) while in some cases the backsheet 50 may not permit vapors to escape (i.e., non-breathable). Thus, the backsheet 50 may comprise a polymeric film such as thermoplastic films of polyethylene or polypropylene. A suitable material for the backsheet 50 is a thermoplastic film having a thickness of from about 0.012 mm (0.5 mil) to about 0.051 mm (2.0 mils), for example Any suitable backsheet known in the art may be utilized with the present invention.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness.

The absorbent core 40 of the present disclosure may comprise any suitable shape including but not limited to an oval, a discorectangle, a rectangle, an asymmetric shape, and an hourglass. For example, in some forms of the present invention, the absorbent core 40 may comprise a contoured shape, e.g. narrower in the intermediate region than in the end regions. As yet another example, the absorbent core may comprise a tapered shape having a wider portion in one end region of the pad which tapers to a narrower end region in the other end region of the pad. The absorbent core 40 may comprise varying stiffness in the MD and CD.

The configuration and construction of the absorbent core 40 may vary (e.g., the absorbent core 40 may have varying caliper zones, a hydrophilic gradient, a superabsorbent gradient, or lower average density and lower average basis weight acquisition zones). Further, the size and absorbent capacity of the absorbent core 40 may also be varied to accommodate a variety of wearers. However, the total absorbent capacity of the absorbent core 40 should be compatible with the design loading and the intended use of the disposable absorbent article 10.

In some forms of the present invention, the absorbent core 40 may comprise a plurality of multi-functional layers that are in addition to the first and second laminates. For example, the absorbent core 40 may comprise a core wrap (not shown) useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself.

The absorbent core 40 of the present disclosure may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen. These may be used to configure the superabsorbent layers. The absorbent core comprises a storage layer which can contain conventional absorbent materials. In addition to conventional absorbent materials such as creped cellulose wadding, fluffed cellulose fibers, Rayon fibers, wood pulp fibers also known as airfelt, and textile fibers, the storage layer often includes superabsorbent polymer material that imbibes fluids and form hydrogels. Such materials are also known as absorbent gelling materials ("AGM", herein after) and may be included in particle form. AGM is typically capable of absorbing large quantities of body fluids and retaining them under moderate pressures. Synthetic fibers including cellulose acetate, polyvinyl fluoride, polyvinylidene chloride, acrylics (such as ORLON), polyvinyl acetate, non-soluble polyvinyl alcohol, polyethylene, polypropylene, polyamides (such as nylon), polyesters, bicomponent fibers, tricomponent fibers, mixtures thereof and the like can also be used in the secondary storage layer. The storage layer can also include filler materials, such as PERLITE, diatomaceous earth, VERMICULITE, or other suitable materials, that lower rewet problems.

The storage layer may have AGM in a uniform distribution or may have AGM in a non-uniform distribution. The AGM may be in the in the form of channels, pockets, stripes, criss-cross patterns, swirls, dots, or any other pattern, either two or three dimensional, that can be imagined by man. The AGM may be sandwiched between a pair of fibrous cover layers. Or AGM may be encapsulated, at least in part, by a single fibrous cover layer.

Portions of the storage layer can be formed only of AGM or can be formed of AGM dispersed in a suitable carrier such as cellulose fibers in the form of fluff or stiffened fibers. One example of a non-limiting storage layer is a first layer formed only of superabsorbent material that is disposed on a second layer that is formed from a dispersion of superabsorbent material within cellulose fibers.

The absorbent article 10 may further comprise barrier cuffs.

Test Methods

1. Nonwoven Sample Preparation

If a nonwoven is available in its raw material form, a specimen with the size about 25 mm×25 mm or a bigger size is cut from the raw material to include at least one complete a protruded first area and part of two adjacent second areas. If a nonwoven is a component layer such as a secondary topsheet of an absorbent article, the absorbent article this size is cut and the nonwoven layer is removed from the absorbent article, using a razor blade to excise the nonwoven layer from the underling layers of the absorbent article. A cryogenic spray (such as Cyto-Freeze, Control Company, Houston TX) or other suitable solvents that do not permanently alter the properties of the nonwoven layer composition may be used to remove the nonwoven layer specimen from the underling layers if necessary. Any remaining adhesive may be removed from the specimen by the following steps using Tetrahydrofuran (THF) as solvent.

1) In a hood, transfer 1 liter of THF into the 3-4 liter beaker.
2) Submerge specimen in the 1 liter of THF.
3) Place beaker on shaking table and stir gently for 15 minutes and keep solution with sample sit for 5 additional minutes.

4) Take specimen out of THF solution, and carefully squeeze THF solution out of specimen.
5) Let specimen air dry in hood for a minimum of 15 minutes.

To obtain a nonwoven cross section specimen, the nonwoven is laid on a flat bench with a first side upward, and is cut to expose a cross section of the specimen.

2. Caliper and Caliper Factor 2.1 Caliper

The caliper, or thickness, of a test specimen is measured as the distance between a reference platform on which the specimen rests and a pressure foot that exerts a specified amount of pressure onto the specimen over a specified amount of time. All measurements are performed in a laboratory maintained at 23° C.±2 C.° and 50%±2% relative humidity and test specimens are conditioned in this environment for at least 2 hours prior to testing.

Caliper is measured with a manually-operated micrometer equipped with a pressure foot capable of exerting a steady pressure of 0.50 kPa±0.01 kPa onto the test specimen. The manually-operated micrometer is a dead-weight type instrument with readings accurate to 0.01 mm. A suitable instrument is Mitutoyo Series 543 ID-C Digimatic, available from VWR International, or equivalent. The pressure foot is a flat ground circular movable face with a diameter that is smaller than the test specimen and capable of exerting the required pressure. A suitable pressure foot has a diameter of 25.4 mm, however a smaller or larger foot can be used depending on the size of the specimen being measured. The test specimen is supported by a horizontal flat reference platform that is larger than and parallel to the surface of the pressure foot. The system is calibrated and operated per the manufacturer's instructions.

Obtain a test specimen by removing it from an absorbent article, if necessary. When excising the test specimen from an absorbent article, use care to not impart any contamination or distortion to the test specimen layer during the process. The test specimen is obtained from an area free of folds or wrinkles, and it must be larger than the pressure foot.

To measure caliper, first zero the micrometer against the horizontal flat reference platform. Place the test specimen on the platform with the test location centered below the pressure foot. Gently lower the pressure foot with a descent rate of 3.0 mm±1.0 mm per second until the full pressure is exerted onto the test specimen. Wait 5 seconds and then record the caliper of the test specimen to the nearest 0.001 mm. In like fashion, repeat for a total of ten replicate test specimens. Calculate the arithmetic mean for all caliper measurements and report as Caliper to the nearest 0.001 mm.

2.2 Caliper Factor

The caliper factor, as mentioned previously is the caliper per 10 gsm of basis weight of the sample. So, the equation is caliper/(basis weight/10).

At least 10 replica of a sample are tested and an average value (arithmetic mean) of the at least 10 replica is reported as caliper factor.

3. Basis Weight

The basis weight of a test sample is the mass (in grams) per unit area (in square meters) of a single layer of material and is measured in accordance with compendial method WSP 130.1. The mass of the test sample is cut to a known area, and the mass of the sample is determined using an analytical balance accurate to 0.0001 grams. All measurements are performed in a laboratory maintained at 23° C.±2

C.° and 50%±2% relative humidity and test samples are conditioned in this environment for at least 2 hours prior to testing.

Measurements are made on test samples taken from rolls or sheets of the raw material, or test samples obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained. The test specimen must be as large as possible so that any inherent material variability is accounted for.

Measure the dimensions of the single layer test specimen using a calibrated steel metal ruler traceable to NIST, or equivalent. Calculate the Area of the test specimen and record to the nearest 0.0001 square meter. Use an analytical balance to obtain the Mass of the test specimen and record to the nearest 0.0001 gram. Calculate Basis Weight by dividing Mass (in grams) by Area (in square meters) and record to the nearest 0.01 grams per square meter (gsm). In like fashion, repeat for a total of ten replicate test specimens. Calculate the arithmetic mean for Basis Weight and report to the nearest 0.01 grams/square meter.

4. Material Compositional Analysis

The quantitative chemical composition of a test specimen comprising a mixture of fiber types is determined using ISO 1833-1. All measurements are performed in a laboratory maintained at 23° C.±2 C.° and 50%±2% relative humidity.

Analysis is performed on test samples taken from rolls or sheets of the raw material, or test samples obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained and tested as per ISO 1833-1 to quantitatively determine its chemical composition.

5. Fiber Decitex (Dtex)

Textile webs (e.g. woven, nonwoven, airlaid) are comprised of individual fibers of material. Fibers are measured in terms of linear mass density reported in units of decitex. The decitex value is the mass in grams of a fiber present in 10,000 meters of that fiber. The decitex value of the fibers within a web of material is often reported by manufacturers as part of a specification. If the decitex value of the fiber is not known, it can be calculated by measuring the cross-sectional area of the fiber via a suitable microscopy technique such as scanning electron microscopy (SEM), determining the composition of the fiber with suitable techniques such as FTIR (Fourier Transform Infrared) spectroscopy and/or DSC (Dynamic Scanning calorimetry), and then using a literature value for density of the composition to calculate the mass in grams of the fiber present in 10,000 meters of the fiber. All testing is performed in a room maintained at a temperature of 23° C.±2.0° C. and a relative humidity of 50%±2% and samples are conditioned under the same environmental conditions for at least 2 hours prior to testing.

If necessary, a representative sample of web material of interest can be excised from an absorbent article. In this case, the web material is removed so as not to stretch, distort, or contaminate the sample.

SEM images are obtained and analyzed as follows to determine the cross-sectional area of a fiber. To analyze the cross section of a sample of web material, a test specimen is prepared as follows. Cut a specimen from the web that is about 1.5 cm (height) by 2.5 cm (length) and free from folds or wrinkles. Submerge the specimen in liquid nitrogen and fracture an edge along the specimen's length with a razor blade (VWR Single Edge Industrial Razor blade No. 9, surgical carbon steel). Sputter coat the specimen with gold and then adhere it to an SEM mount using double-sided conductive tape (Cu, 3M available from electron microscopy sciences). The specimen is oriented such that the cross section is as perpendicular as possible to the detector to minimize any oblique distortion in the measured cross sections. An SEM image is obtained at a resolution sufficient to clearly elucidate the cross sections of the fibers present in the specimen. Fiber cross sections may vary in shape, and some fibers may consist of a plurality of individual filaments. Regardless, the area of each of the fiber cross sections is determined (for example, using diameters for round fibers, major and minor axes for elliptical fibers, and image analysis for more complicated shapes). If fiber cross sections indicate inhomogeneous cross-sectional composition, the area of each recognizable component is recorded and dtex contributions are calculated for each component and subsequently summed. For example, if the fiber is bi-component, the cross-sectional area is measured separately for the core and sheath, and dtex contribution from core and sheath are each calculated and summed. If the fiber is hollow, the cross-sectional area excludes the inner portion of the fiber comprised of air, which does not appreciably contribute to fiber dtex. Altogether, at least 100 such measurements of cross-sectional area are made for each fiber type present in the specimen, and the arithmetic mean of the cross-sectional area $\alpha_k$ for each are recorded in units of micrometers squared ($\mu m^2$) to the nearest 0.1 $\mu m^2$.

Fiber composition is determined using common characterization techniques such as FTIR spectroscopy. For more complicated fiber compositions (such as polypropylene core/polyethylene sheath bi-component fibers), a combination of common techniques (e.g. FTIR spectroscopy and DSC) may be required to fully characterize the fiber composition. Repeat this process for each fiber type present in the web material.

The decitex $d_k$ value for each fiber type in the web material is calculated as follows:

$$d_k = 10000\,\text{m} \times a_k \times \rho_k \times 10^{-6}$$

where $d_k$ is in units of grams (per calculated 10,000 meter length), $\alpha_k$ is in units of $\mu m^2$, and $\rho_k$ is in units of grams per cubic centimeter (g/cm$^3$). Decitex is reported to the nearest 0.1 g (per calculated 10,000 meter length) along with the fiber type (e.g. PP, PET, cellulose, PP/PET bico).

6. Artificial Menstrual Fluid (AMF) Preparation

The Artificial Menstrual Fluid (AMF) is composed of a mixture of defibrinated sheep blood, a phosphate buffered saline solution and a mucous component. The AMF is prepared such that it has a viscosity between 7.15 to 8.65 centistokes at 23° C.

Viscosity of the AMF is performed using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and instrument is operated and calibrated as per the manufacturer. Measurements are taken at 23° C.±1 C.° and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, OH, or equivalent), gastric mucin with a viscosity target of 3-4 centistokes when prepared as a 2% aqueous solution (crude form, available from Sterilized American Laboratories, Inc., Omaha, NE, or equivalent), 10% v/v lactic acid aqueous solution, 10% w/v potassium hydroxide aqueous solution, sodium phosphate dibasic anhydrous (reagent grade), sodium chloride (reagent grade), sodium phosphate monobasic monohydrate (reagent grade) and deionized water, each available from VWR International or equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add deionized water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add deionized water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5 C°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1 C°.

Allow the temperature of the sheep blood and mucous component to come to 23° C.±1 C°. Using a 500 mL graduated cylinder, measure the volume of the entire batch of the previously prepared mucous component and add it to a 1200 mL beaker. Add an equal volume of sheep blood to the beaker and mix thoroughly. Using the viscosity method previously described, ensure the viscosity of the AMF is between 7.15-8.65 centistokes. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 C°. Any unused portion is discarded after testing is complete.

7. Acquisition Time

Acquisition time is measured for an absorbent article loaded with Artificial Menstrual Fluid (AMF) as described herein, using a strikethrough plate and an electronic circuit interval timer. The time required for the absorbent article to acquire a dose of AMF is recorded. All measurements are performed in a laboratory maintained at 23° C.±2 C.° and 50%±2% relative humidity.

Referring to FIGS. 7A-7E, the strikethrough plate 9001 is constructed of Plexiglas with an overall dimension of 10.2 cm long by 10.2 cm wide by 3.2 cm tall. A longitudinal channel 9007 running the length of the plate is 13 mm deep and 28 mm wide at the top plane of the plate, with lateral walls that slope downward at 65° to a 15 mm wide base. A central test fluid well 9009 is 26 mm long, 24 mm deep and 38 mm wide at the top plane of the plate with lateral walls that slope downward at 65° to a 15 mm wide base. At the base of the test fluid well 9009, there is an "H" shaped test fluid reservoir 9003 open to the bottom of the plate for fluid to be introduced onto the underlying article. The test fluid reservoir 9003 has an overall length ("L") of 25 mm, width ("W") of 15 mm, and depth ("D") of 8 mm. The longitudinal legs of the reservoir are 4 mm wide and have rounded ends with a radius 9010 of 2 mm. The legs are 3.5 mm apart. The central strut has a radius 9011 of 3 mm and houses the opposing electrodes 9004 6 mm apart. The lateral sides of the reservoir bow outward at a radius 9012 of 14 mm bounded by the overall width, W, of 15 mm Two wells 9002 (80.5 mm long×24.5 mm wide×25 mm deep) located outboard of the lateral channel, are filled with lead shot to adjust the overall mass of the plate to provide a constraining pressure of 0.25 psi (17.6 gf/cm$^2$) to the test area. Electrodes 9004 are embedded in the plate 9001, connecting the exterior banana jacks 9006 to the inside wall of the fluid reservoir 9003. A circuit interval timer is plugged into the jacks 9006 to the inside wall 9005 of the fluid reservoir 9003. A circuit interval timer (not shown in the drawings) is plugged into the jacks 9006, and monitors the impedance between the two electrodes 9004, and measures the time from introduction of the AMF into reservoir 9003 until the AMF drains from the reservoir. The timer has a resolution of 0.01 sec.

Test products are removed from all packaging using care not to press down or pull on the products while handling. No attempt is made to smooth out wrinkles. The test samples are conditioned at 23° C.±2 C.° and 50%±2% relative humidity for at least 2 hours prior to testing.

The required mass of the strikethrough plate must be calculated for the specific dimensions of the test article such that a confining pressure of 1.72 kPa is applied. Determine the longitudinal and lateral midpoint of the article's absorbent core. Measure and record the lateral width of the core to the nearest 0.1 cm. The required mass of the strikethrough plate is calculated as the core width multiplied by strikethrough plate length (10.2 cm) multiplied by 17.6 gf/cm$^2$ and recorded to the nearest 0.1 g. Add lead shot to the plate to achieve the calculated mass.

Connect the electronic circuit interval timer to the strikethrough plate 9001 and zero the timer. Place the test product onto a flat, horizontal surface with the body side facing up. Gently place the strikethrough plate 9001 onto the center of the test product ensuring that the "H" shaped reservoir 9003 is centered over the test area.

Using a mechanical pipette, accurately pipette 3.00 mL±0.05 mL of AMF into the test fluid reservoir 9003. The fluid is dispensed, without splashing, along the molded lip of the bottom of the reservoir 9003 within a period of 3 seconds or less. After the fluid has been acquired, record the acquisition time to the nearest 0.01 second. Thoroughly clean the electrodes 9004 before each test.

In like fashion, a total of three (3) replicate samples are tested for each test product to be evaluated. Report the Acquisition Time (sec) as the mean of the replicates to the nearest 0.01 sec.

8. Rewet

Light pressure rewet is measured for an absorbent article loaded with Artificial Menstrual Fluid (AMF) as described herein. The fluid amount left on topsheet, i.e rewet under 0.1 psi pressure is measured after 3.0 gram and 12.0 gram AMF is dispensed. All measurements are performed in a laboratory maintained at 23° C.±2 C.° and 50%±2% relative humidity. Test products are removed from all packaging using care not to press down or pull on the products while handling. No attempt is made to smooth out wrinkles. The test samples are conditioned at 23° C.±2 C.° and 50%±2% relative humidity for at least 2 hours prior to testing.

The required mass (to the nearest 0.01 gram) of the plate must be calculated for the specific dimensions of the test article such that a confining pressure of 0.1 psi pressure is applied. Determine the longitudinal and lateral midpoint of absorbent article. Measure and record the lateral width of the absorbent article to the nearest 0.1 cm.

Place the test product onto a flat, horizontal surface with the body side facing up. Place a test vial on a balance, zero it. Use a pipette to add 3.00 gram into the vial and weigh to the nearest 0.01 gram. Then carefully dispense the fluid onto the center of the test articles. Wait for 3 min.

Place 4-6 pieces of known weight filter paper (termed as "dry weight") (a typical lab filter paper, for example, Ahlstrom #632 12.7 cm×12.7 cm filter papers) on top of the center fluid area. Apply the required mass to generate 0.1 psi pressure, keep it under pressure for 5 seconds.

Weigh the filter papers again (termed as "wet weight"). The difference between the wet weight and dry weight of the filter paper is the light pressure rewet at the added amount of fluid.

Repeat the test step till 12.00 gram fluid are dispensed on the absorbent article.

In like fashion, a total of three (3) to six (6) replicates samples are tested for each test product to be evaluated. Report the light pressure rewet as the arithmetic mean of the replicates to the nearest 0.01 gram.

9. Vertical Wicking Height

Vertical wicking height of a nonwoven is measured according to INDA/EDANA STANDARD TEST: WSP 10.1 (05) "7.3 The liquid wicking rate (capillarity))". 6 replica for each sample are tested and an average value (arithmetic mean) of the 6 replica is reported as vertical wicking height.

10. Relative Shape Factor in Radius

Figure 6:
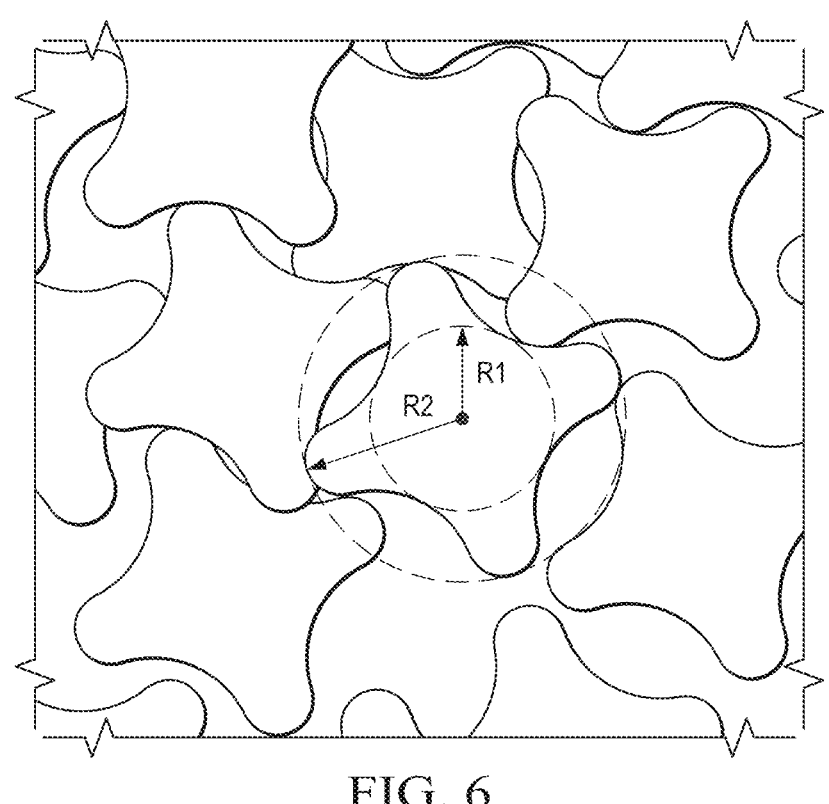
FIG. 6 is a schematic representation of fibers to illustrate measurement of a relative shape factor in radius of a fiber.
Figure 7A:
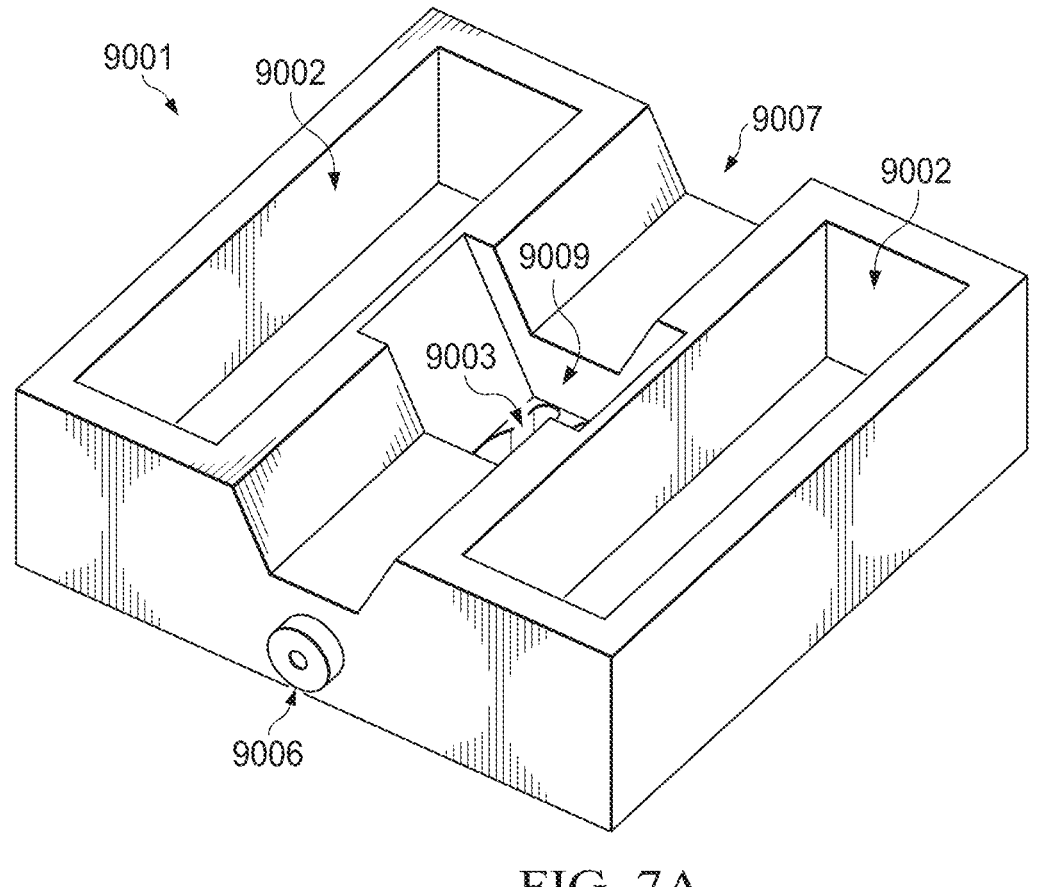
FIG. 7A is a perspective view of a strikethrough plate for acquisition time measurement.
Figure 7B:
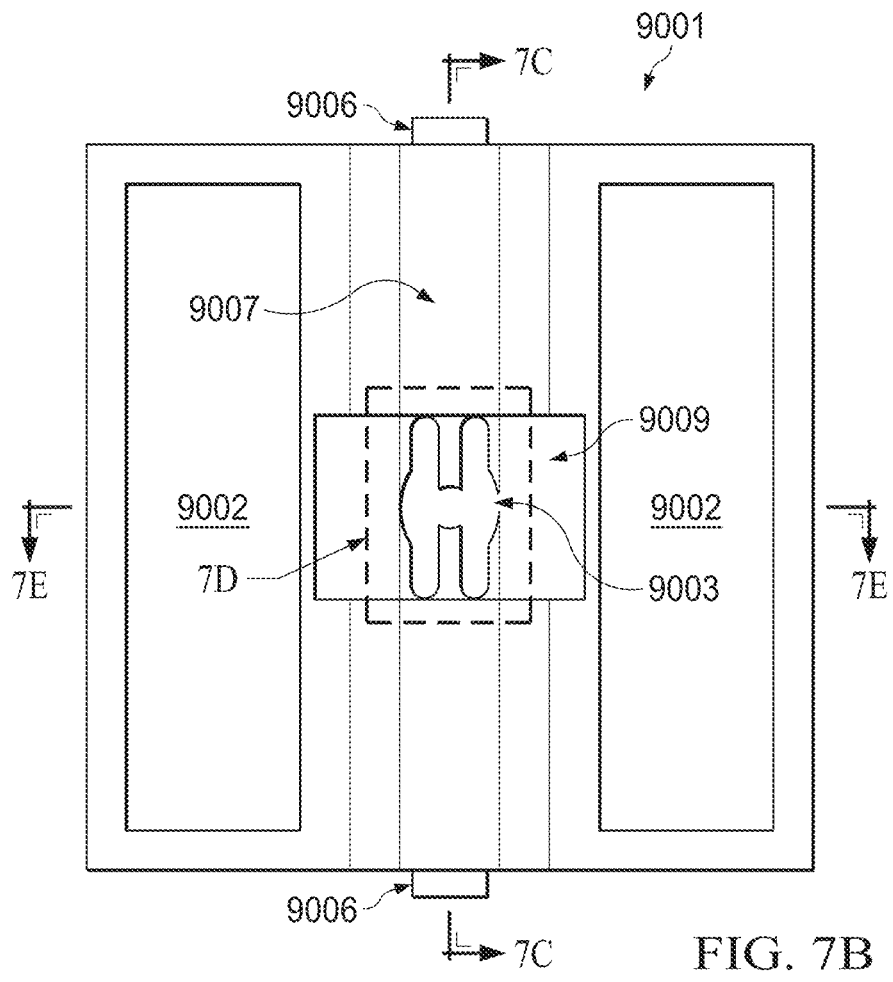
FIG. 7B is a plan view of the strikethrough plate of FIG. 7A.
Figure 7C:
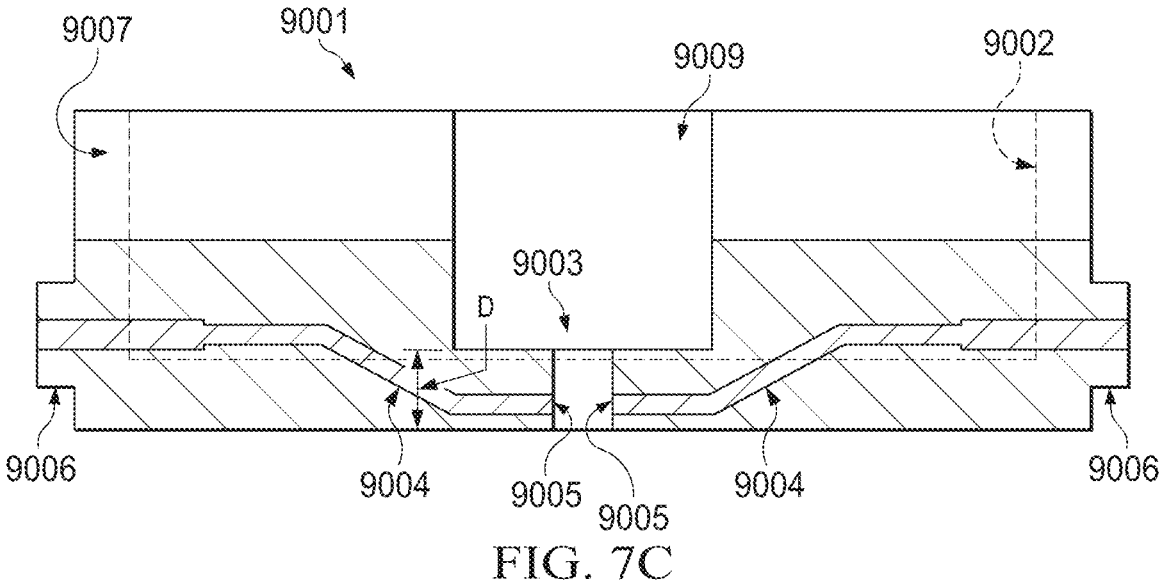
FIG. 7C is a plan view of a 7C-7C direction cross section of the strikethrough plate of FIG. 7B.
Figures 7D, 7E:
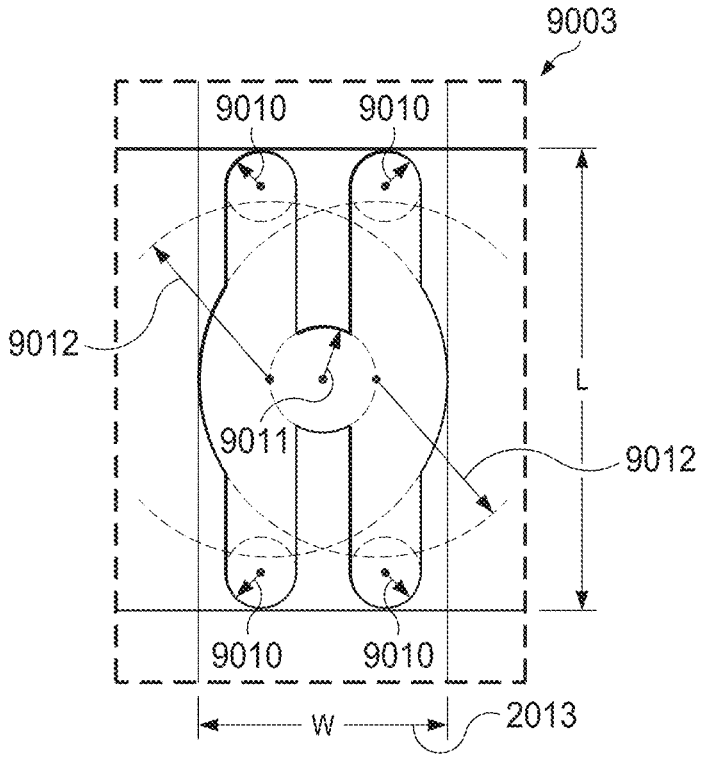
FIG. 7D is a plan view of part of the strikethrough plate of FIG. 7B.
FIG. 7E is a plan view of a 7E-7E direction cross section of the strikethrough plate of FIG. 7B.

SEM images of perpendicular cross sections of fibers are obtained and analyzed as follows to determine Relative Shape Factor in Radius ("RSFR") of fibers. Fibers to be analyzed are selected at random. Referring to FIG. 6, for each fiber analyzed, two circles are drawn. The first is the smallest circle that circumscribes the entirety of the fiber cross section, and R1 is defined as this first circle's radius. The second is the largest circle that can be inscribed entirely within the fiber cross section, and R2 is defined as this second circle's radius.

The RSFR of the fiber is calculated as follows:

$$RSFR = \left(1 - \frac{R2}{R1}\right) \times 100\%$$

At least 10 replica of a sample fibers are tested and an average value (arithmetic mean) of the at least 10 replica to the nearest 0.1% is reported as RSFR of the fiber.

11. Air Permeability

Air permeabilities of an original nonwoven and a wet and re-dried nonwoven are tested. A wet and re-dried sample are prepared as follows:

Place the sample nonwoven into a basin with sufficient distilled water so that the fluid completely covers the sample nonwoven. Submerge the sample nonwoven in the water and stay for 5 min for the sample nonwoven to completely absorb the water. Take out the sample nonwoven using a holder from the water and let it dry naturally for 24 h in laboratory maintained at 23±2° C. and 50±2% relative humidity.

All measurements are performed in a laboratory maintained at 23±2° C. and 50±2% relative humidity and test specimens are conditioned in this environment for at least 2 hours prior to testing.

The Air Permeability of a substrate is determined according to INDA/EDANA Nonwovens Standard Procedures NWSP 070.1.R0 (15) making use of a Textest FX3300 (Textest Instruments, Schwerzenbach, Switzerland) air permeability tester or equivalent. A circular test head with an area of 38 cm$^2$ is used, and while a fixed pressure of 125 Pa is maintained across the specimen, air flow through the specimen is measured in cubic meter per square meter per minute (m$^3$/m$^2$/min). Twelve rectangular specimens of the material (original material, and wet and re-dried sample) are taken such that each specimen center corresponds to the center of the material and such that the length and width of each specimen are greater than the smallest dimension of the circular head. The specimen is placed under the test head such that the center of the specimen is matching the center of the test head. The five lower specimens are analyzed in this way, and the air permeability of each is recorded in m$^3$/m$^2$/min to the nearest 1 m$^3$/m$^2$/min. The arithmetic mean of the individual specimen results is calculated and reported as the Air Permeability in units m³/m²/min to the nearest 1 m³/m²/min.

EXAMPLES

Example 1

A plurality of nonwovens for fluid management layers were constructed and tested. For each of examples, the following Table 1 was their constituent material makeup. All of the nonwoven substrates were hydroentangled, spunlaced.

Figure 4:
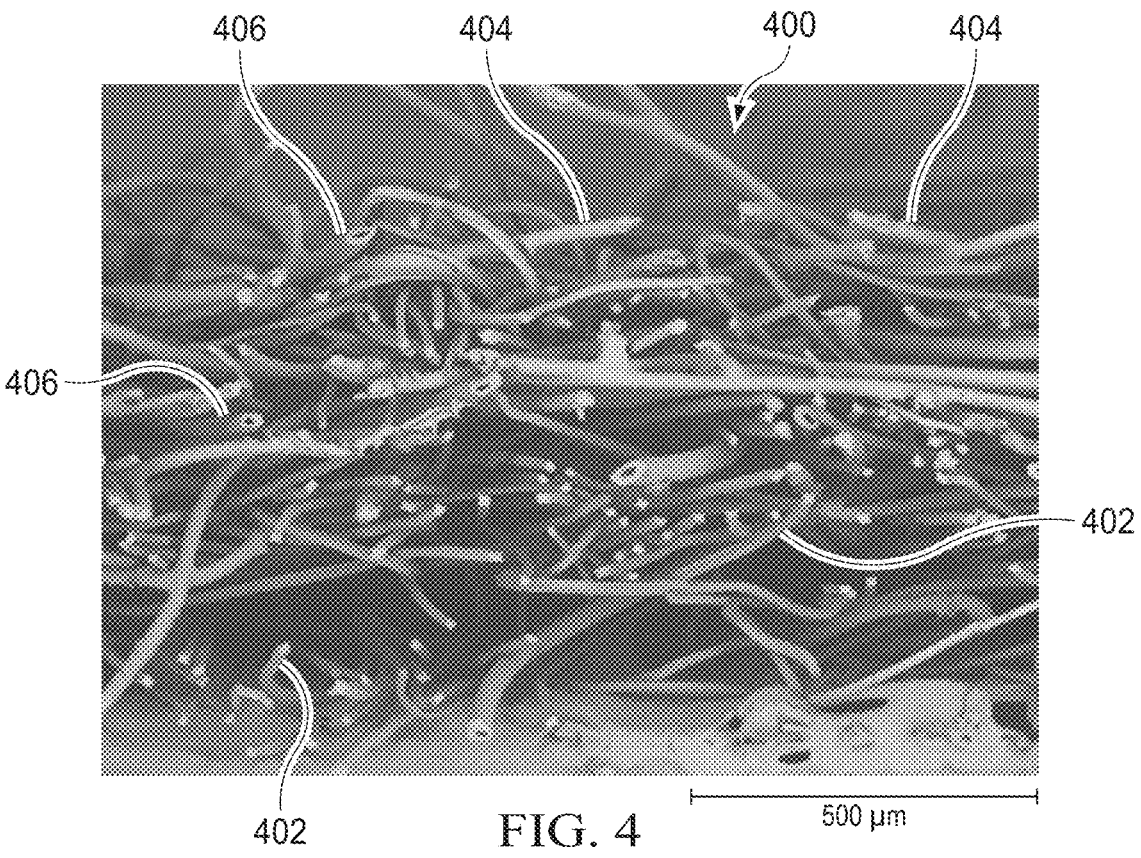
FIG. 4 is an SEM image showing a cross section of a fluid management layer according to the present invention.
Figure 5:
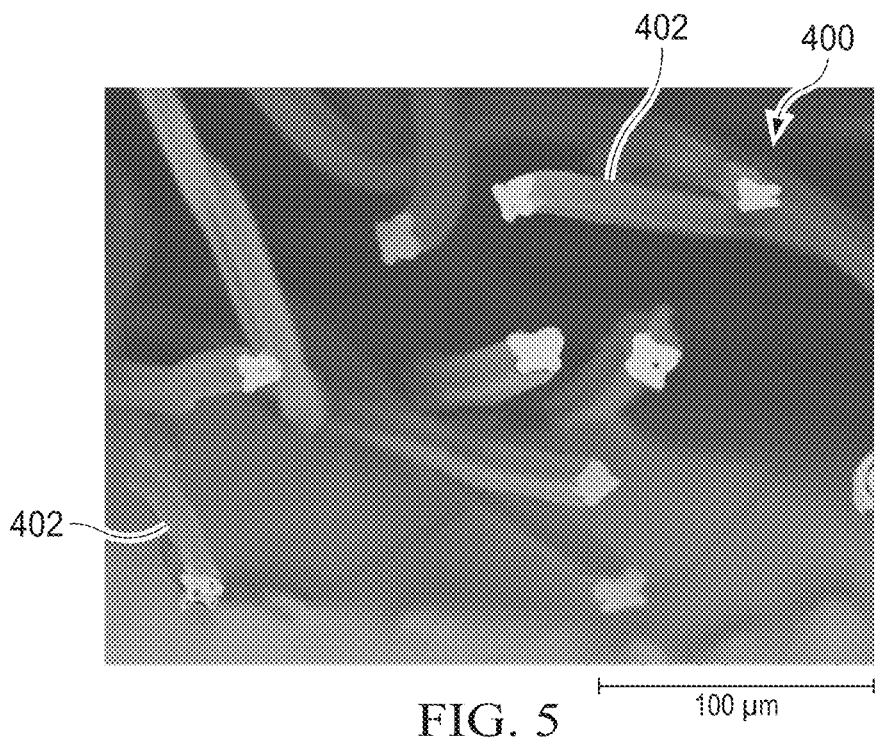
FIG. 5 is an SEM image showing a cross section of a fluid management layer according to the present invention

FIGS. 4 and 5 are scanning electron microscope images of Nonwoven 1. Referring to FIG. 4, Nonwoven 1 400 contains non-swelling wicking fibers (1. dtex X-shaped PET fibers in this case) 402, stiffening fibers (5.5 dtex PE/PET core/sheath bicomponent fibers in this case) 404, and resilient fibers (10 dtex FENC hollow spiral PET fibers in this case) 406. FIG. 5 is an enlarged image of scanning electron microscope images of Nonwoven 1 which shows the non-swelling wicking fiber more clearly.

RSFR of 1.5 dtex X-Shaped PET fibers was tested according to the Relative Shape Factor in Radius test under the Test Methods. 17 replica of the fiber was tested, and got an RSFR value of 41.8%.

For the caliper factor, calipers of 48 replica of each sample were tested and an average value of the 48 replica was reported as caliper factor.

Vertical wicking heights of Nonwovens 1-7 were measure accruing to Vertical Wicking Height test under the Test Methods.

TABLE 1

| | Non-woven 1 | Non-woven 2 | Non-woven 3 | Non-woven 4 | Non-woven 5 | Non-woven 6 | Non-woven 7 |
|---|---|---|---|---|---|---|---|
| 1$^{st}$ web (gsm) | 18 | 24 | 28 | 28 | 18 | 18 | 27 |
| 1.7 dtex viscose | 0.0 | 10.8 (45.0) | 11.2 (40.0) | 5.6 (20.0) | 14.4 (80.0) | | |
| 1.5 dtex X-Shaped PET (gsm) (%) | 14.4 (80.0) | 8.4 (35.0) | 0.0 (0.0) | 0.0 (0.0) | 0.0 (0.0)) | | |
| 1.5 dtex round PBT (gsm) (%) | | | | | | 14.4 (80.0) | |
| 1.7 dtex PE/PP bico (gsm) (%) | 0.0 (0.0) | 0.0 (0.0) | 11.2 (40.0) | 0.0 (0.0 | 0.0 (0.0) | | |
| 2.2 dtex PE/PET bico (gsm) (%) | 0.0 (0.0) | 0.0 (0.0) | 0.0 (0.0) | 14 (50.0) | 0.0 (0.0) | | |
| 5.5 dtex PE/PET bico (gsm) (%) | 0.0 (0.0) | 4.8 (20.0) | 0.0 (0.0) | 0.0 (0.0) | 0.0 (0.0) | 3.6 (20.0) | |
| 6.6 dtex trilobal PET (gsm) (%) | | | | | | | 13.5 (50) |
| 6.6 dtex pentagonal PET (gsm) (%) | | | | | | | 13.5 (50) |
| 4.4 dtex PET (gsm) (%) | 0.0 (0.0) | 0.0 (0.0) | 5.6 (20.0) | 0.0 (0.0) | 0.0 (0.0) | | |
| 10 dtex hollow spiral PET (gsm) (%) | 3.6 (20.0) | 0.0 (0.0) | 0.0 (0.0) | 8.4 (30.0) | 3.6 (20.0) | | |
| 2nd web(gsm) | 37 | 31 | 27 | 27 | 37 | 37 | 28 |
| 1.7 dtex viscose (gsm) (%) | 0.0 (0.0) | 7.7 (24.8) | 10.8 (40.0) | 5.4 (20.0) | 9.25 (25.0) | | |
| 1.5 dtex PET X-Shaped (gsm) (%) | 9.25 (25.0) | 0.0 (0.0) | 0.0 (0.0) | 0.0 (0.0) | 0.0 (0.0) | | |
| 1.5 dtex round PBT (gsm) (%) | | | | | | 37 (100) | |
| 1.7 dtex PE/PP bico (gsm) (%) | 0.0 (0.0) | 0.0 (0.0) | 10.8 (40.0) | 0.0 (0.0) | 0.0 (0.0) | | |
| 2.2 dtex PE/PET bico (gsm) (%) | 0.0 (0.0) | 0.0 (0.0) | 0.0 (0.0) | 13.5 (50) | 0.0 (0.0) | | |
| 5.5 dtex PE/PET bico (gsm) (%) | 16.65 (45.0) | 15.5 (50.0) | 0.0 (0.0) | 0.0 (0.0) | 16.65 (45.0) | | |
| 4.4 dtex PET fiber (gsm) (%) | 0.0 (0.0) | 0.0 (0.0) | 5.4 (20.0) | 0.0 (0.0) | 0.0 (0.0) | | |
| 6.6 dtex trilobal PET (gsm) (%) | | | | | | | 14 (50) |
| 6.6 dtex pentagonal PET (gsm) (%) | | | | | | | 14 (50) |
| 10 dtex hollow spiral PET (gsm) (%) | 11.1 (30.0) | 7.8 (25.2) | 0.0 (0.0) | 8.1 (30.0) | 11.1 (30.0) | | |
| Total basis weight (gsm) | 55 | 55 | 55 | 55 | 55 | 55 | 55 |
| Caliper factor | 0.13 | 0.11 | 0.10 | 0.15 | 0.13 | 0.09 | 0.15 |
| Vertical wicking height (mm)  1 min | 47.0 | | | | 58.7 | | |
| 3 min | 62.0 | | | | 68.0 | | |
| 5 min | 69.3 | 55.6 | 68.0 | 37.6 | 80.0 | 76.0 | 45.0 |

1.5 dtex X-Shaped PET: Far Eastern New Century Corporation
1.7 dtex PE/PP bico: Toray Advanced Materials Korea Inc.
2.2 dtex PE/PET bico: Jiangsu Jiangnan High Polymer Fiber Co., Ltd
5.5 dtex PE/PET bico: Jiangsu Jiangnan High Polymer Fiber Co., Ltd
4.4 dtex PET fiber: Sinopec Yizheng Chemical Fiber Co., Ltd
10 dtex hollow spiral PET: Far Eastern New Century Corporation Nonwovens 1 and 2, inventive nonwovens, have high caliper factors and exhibit high vertical wicking height values even in prolonged time (at 5 min). A high vertical wicking height value may explain a low rewet value in the absorbent article of the present invention.

Nonwovens 3 and 5, comparative nonwovens, which do not include non-swelling wicking fibers exhibit vertical wicking height value significantly lower than the inventive nonwovens.

Nonwoven 6, a comparative nonwoven, which contains 1.5 dtex round PBT fibers instead of non-swelling wicking fibers, and insufficient amount of stiffening fibers and resilient fibers has a relatively low caliper factor.

Nonwoven 7, a comparative nonwoven, which contains non-swelling synthetic fibers in a high dtex exhibits a vertical wicking height value significantly lower than the inventive nonwovens.

Air permeabilities of Nonwoven 1 and Nonwoven 3 at two conditions, original condition, and wet and re-dried condition were tested according to Air permeability test under the Test Methods, and are indicated in Table 2 below.

TABLE 2

| | Nonwoven 1 | Nonwoven 3 |
|---|---|---|
| Air permeability (original) (m³/m²/min) | 163.9 (SD*: 4.85) | 137.9 (SD: 5.53) |
| Air permeability (wet and re-dried) (m³/m²/min) | 166 (SD: 5.31) | 129.8 (SD: 5.08) |

SD*: standard deviation

Nonwoven 1 shows substantially no change in air permeability values in the original condition and the wet and re-dried condition which confirms that there is no substantial change in pores size and channels in the nonwoven. Nonwoven 3 shows a noticeable drop in air permeability at the wet and re-dried condition compared to the original condition which reflects pore sizes and channels in the nonwoven are decreased maybe due to the present of high amount of absorbent fibers.

Example 2

Disposable absorbent articles comprising fluid management layers according to the present invention were constructed and tested. Additionally, a plurality of disposable absorbent articles comprising comparative fluid management layers were constructed and tested. The difference among samples was solely the fluid management layer as shown in Table 3 below. Samples 1 and 2 are inventive samples and Samples 3-7 are comparison samples. Inventive samples comprised a fluid management layer of the present disclosure while the comparative sample absorbent articles comprised comparative fluid management layers. For each of inventive samples and comparative samples, the following components were utilized.

Topsheet—The topsheet for each of the inventive and comparative samples was a 24 gsm carded air-through nonwoven made of 60% of hydrophilic PE/PET bicomponent fibers and 40% of hydrophobic PE/PET bicomponent fibers. The nonwoven is available from Yanjan, China.

Absorbent Core—The absorbent core was 145 gsm MBAL core comprising pulp fibers, absorbent gelling material, and bico fibers, available from Fitesa, China.

TABLE 3

| | Sample 1 | Sample 2 | Sample 3 | Sample 4 | Sample 5 | Sample 6 | Sample 7 |
|---|---|---|---|---|---|---|---|
| Fluid handling layer | Non-woven 1 | Non-woven 2 | Non-woven 3 | Non-woven 4 | Non-woven 5 | Non-woven 6 | Non-woven 7 |

Acquisition time and rewet of each sample were measured according to the Acquisition Time test and the Rewet test under Test Methods above, respectively, and results are indicated in Table 4.

TABLE 4

| | | Sample 1 | Sample 2 | Sample 3 | Sample 4 | Sample 5 | Sample 6 | Sample 7 |
|---|---|---|---|---|---|---|---|---|
| Acquisition time at 0.25 psi/s | 3 ml | 16.75 | 20.46 | 22.8 | 22.29 | 21.40 | 22.92 | 14.63 |
| | 6 ml | 46.74 | 46.30 | 66.1 | 50.55 | 53.45 | 55.79 | 26.74 |
| | 9 ml | 53.81 | 61.39 | 101.1 | 63.60 | 79.55 | 84.49 | 36.72 |
| | 12 ml | 63.06 | 67.83 | 130.0 | 75.24 | 96.72 | 104.04 | 35.89 |
| Rewet at 0.1 psi/g | 3 ml | 0.00 | 0.00 | 0.004 | 0.04 | 0.01 | 0.00 | 0.04 |
| | 6 ml | 0.03 | 0.02 | 0.01 | 0.04 | 0.01 | 0.02 | 0.08 |
| | 9 ml | 0.14 | 0.17 | 0.03 | 0.27 | 0.12 | 0.07 | 0.47 |
| | 12 ml | 0.41 | 0.40 | 0.06 | 0.47 | 0.30 | 0.15 | 0.69 |

Samples 1 and 2, inventive samples, exhibit high acquisition times even upon repeated liquid insults. In addition, Samples 1 and 2 exhibit low rewet values even upon repeated liquid insults.

Samples 3 and 5, comparative samples, which do not include non-swelling wicking fibers exhibit acquisition times significantly lower than the inventive samples. It is noticed that acquisition times in Samples 3 and 5 significantly increase upon repeated liquid insults.

Sample 4, a comparative sample, which does not include non-swelling wicking fibers exhibit rewet values significantly higher than the inventive samples. It is noticed that rewet values in Sample 3 significantly increases upon repeated liquid insults.

Sample 6, a comparative sample, which contains 1.5 dtex round PBT fibers instead of non-swelling wicking fibers exhibits acquisition times significantly lower than the inventive samples, and the acquisition time significantly increases upon repeated liquid insults.

Sample 7, a comparative sample, which contains 6.6 dtex trilobal PET and 6.6 dtex pentagonal PET fibers very high rewet values. The rewet value significantly increases upon repeated liquid insults.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a skin facing side and a garment facing side, the absorbent article comprising:
   a liquid permeable topsheet, a liquid impermeable backsheet, an absorbent core disposed between the topsheet and the backsheet, and a fluid management layer disposed between the topsheet and the absorbent core,
   wherein the fluid management layer comprises from about 10% to about 60% of non-swelling wicking fibers by weight of the fluid management layer, from about 15% to about 70% of resilient fibers by weight of the fluid management layer, and from about 25% to about 70% of stiffening fibers by weight of fluid management layer as determined by the Material Composition Analysis, and wherein the non-swelling wicking fibers have a relative shape factor in radius in the range of about 25% to about 100% as determined by the Relative Shape Factor in Radius test, and have a linear density of about 0.8 dtex to about 3.3 dtex as determined by the Fiber Decitex test.

2. The absorbent article of claim 1, wherein the fluid management layer further comprises about 1% to about 40% of absorbent fibers by weight of the fluid management layer as determined by the Material Composition Analysis.

3. The absorbent article of claim 1, wherein the non-swelling wicking fibers have a cross section in a shape of cross, trilobal, pentagonal, "H," "Y," "X," "T," or flat ribbon.

4. The absorbent article of claim 1, wherein the fluid management layer comprises a first nonwoven web and a second nonwoven web, the first nonwoven web being closest to the wearer-facing surface in the absorbent article, the percentage of non-swelling wicking fibers in the first nonwoven web by weight of the first nonwoven web and the percentage of non-swelling wicking fibers in the second nonwoven web by weight of the second nonwoven web are different.

5. The absorbent article of claim 1, wherein the non-swelling wicking fibers comprise thermoplastic fibers selected from the group consisting of monocomponent fibers, bicomponent fibers comprising polyolefin resin, and a combination thereof.

6. The absorbent article of claim 1, wherein the resilient fibers have a melting temperature higher than that of the stiffening fibers.

7. The absorbent article of claim 1, wherein the resilient fibers have a linear density of about 4 dtex or higher.

8. The absorbent article of claim 1, wherein fibers in the fluid management layer are integrated.

9. The absorbent article of claim 1, wherein fibers in the fluid management layer are staple fibers.

10. The absorbent article of claim 1, wherein the fluid management layer is spunlaced.

11. The absorbent article of claim 1, wherein the fluid management layer comprises a basis weight of about 20 gsm to about 120 gsm.

12. The absorbent article of claim 1, wherein the absorbent article exhibits an average acquisition speed in a first gush less than about 30 seconds, and in a third gush less than about 60 seconds, when measured in accordance with the Acquisition Time test disclosed herein.

13. A nonwoven sheet comprising from about 10% to about 60% of non-swelling wicking fibers, from about 15% to about 70% of resilient fibers, and from about 25% to about 70% of stiffening fibers by weight of fluid the nonwoven sheet as determined by the Material Composition Analysis, and
   wherein the non-swelling wicking fibers have a relative shape factor in radius in the range of about 25% to about 100% as determined by the Relative Shape Factor in Radius test, and have a linear density of 0.8 dtex to 3.3 dtex as determined by the Fiber Decitex test; and
   wherein the nonwoven sheet comprises substantially no change in air permeability values before and after wetting and re-drying.

14. The nonwoven sheet of claim 13, wherein the nonwoven sheet is spunlaced.

15. An absorbent article having a skin facing side and a garment facing side, the absorbent article comprising:
   a liquid permeable topsheet, a liquid impermeable backsheet, an absorbent core disposed between the topsheet and the backsheet, and a fluid management layer dis-
posed between the topsheet and the absorbent core,
wherein the fluid management layer comprises from about
10% to about 60% of non-swelling wicking fibers by
weight of the fluid management layer, and at least one
of from about 15% to about 70% of resilient fibers by
weight of the fluid management layer and from about
25% to about 70% of stiffening fibers by weight of fluid
management layer as determined by the Material Com-
position Analysis,
wherein the non-swelling wicking fibers have a relative
shape factor in radius in the range of about 25% to
about 100% as determined by the Relative Shape
Factor in Radius test, and have a linear density of about
0.8 dtex to about 3.3 dtex as determined by the Fiber
Decitex test; and
wherein the absorbent article has a rewet at 0.1 psi/g of
less than 0.5 for a 12 mL gush as determined according
to the Rewet test.

16. The absorbent article of claim 1, wherein the non-
swelling wicking fibers comprise polypropylene, polyethyl-
ene terephthalate, and/or polybutylene terephthalate.

17. The absorbent article of claim 1, wherein the non-
swelling wicking fibers comprise bicomponent fibers.

18. The absorbent article of claim 1, wherein the non-
swelling wicking fibers comprise polyethylene terephtha-
late.

19. The absorbent article of claim 1, wherein the non-
swelling wicking fibers comprise a vertical wicking height
of at least 50 mm.

20. The absorbent article of claim 1, wherein the fluid
management layer comprises a caliper factor of at least 0.10.

\* \* \* \* \*